United States Patent [19]
Vermeer et al.

[11] Patent Number: 5,521,293
[45] Date of Patent: May 28, 1996

[54] HETEROATOM CONTAINING ALKYL ALDONAMIDE COMPOUNDS AS SUPERIOR FOAMING, MORE SOLUBLE NONIONIC SURFACTANTS AND A PROCESS FOR THEIR MANUFACTURE

[75] Inventors: Robert Vermeer, Nutley, N.J.; Van Au, New City, N.Y.; Bijan Harichian, South Orange, N.J.

[73] Assignee: Lever Brothers Company, Division of Conopco, Inc., New York, N.Y.

[21] Appl. No.: 436,797

[22] Filed: May 8, 1995

Related U.S. Application Data

[60] Division of Ser. No. 351,929, Dec. 8, 1994, abandoned, which is a continuation-in-part of Ser. No. 981,644, Nov. 25, 1992, abandoned.

[51] Int. Cl.$^6$ ...................................................... C07H 15/04
[52] U.S. Cl. ............................... 536/17.2; 536/53; 536/54
[58] Field of Search .................................. 536/53, 1.1, 4, 536/1, 54, 17.2

[56] References Cited

U.S. PATENT DOCUMENTS

| | | | |
|---|---|---|---|
| 2,662,073 | 12/1953 | Mehltretter et al. | 530/221 |
| 2,721,211 | 10/1955 | Buc | 564/133 |
| 2,752,334 | 6/1956 | Walton | 536/53 |
| 2,776,951 | 1/1957 | Melamed | 526/304 |
| 2,785,152 | 3/1957 | Jones | 530/338 |
| 3,766,267 | 10/1973 | Zak | 564/201 |
| 3,855,290 | 12/1974 | Zak et al. | 564/159 |
| 3,990,991 | 11/1976 | Gerstein | 252/542 |

(List continued on next page.)

FOREIGN PATENT DOCUMENTS

| | | |
|---|---|---|
| 2523962 | 9/1983 | France . |
| 2321752 | 11/1974 | Germany . |
| 2338087 | 1/1975 | Germany . |
| 62-327860 | 7/1989 | Japan . |
| 94/12511 | 6/1994 | WIPO . |

OTHER PUBLICATIONS

Synthetic Emulsifying Agents, Fieser et al., Jun. 20, 1956, vol. 78, pp. 2825–2832.
Linking Sugars with Amino Acid Esters of Lipophilic Alcohols to Form Surface–Active Sugar Derivatives, Geyer, vol. 330 9 (1963), pp. 182–188 (English Translation).
Reaction of Aliphatic Diamines with D–Gluconic Acid δ-Lactone, Geyer, vol. 97 (1964), pp. 2271–2275 (English Translation).
Amphiphilic Properties of Synthetic Glycolipids Based on Amide Linkages, I. Electron Microscopic Studies on Aqueous Gels, Chem. & Physics of Lipids 37 (1985) 227–240.
The Chiral Bilayer Effect Stabilizes Micellar Fibers, Fuhrhop et al., J. Am. Chem. Soc., vol. 109, No. 11; pp. 3386–3390 & Supplemental Material.
Lipid Bilayer Fibers from Diastereomeric and Enantiomeric N–Octylaldonamides, Fuhrhop et al., J. Am. Chem. Soc., 1988, 110, pp. 2861–2867.
Stereochemistry and Curvature Effects in Supramolecular Organization and Separation Process of Micellar N–Alkylaldonamide Mixtures, Fuhrhop et al., J. Am. Chem. Soc., 1990, 112, pp. 1768–1775.
A New Family of Liquid Crystals: N–Substituted Aldonamides, Mol. Cryst. Liq. Cryst. 1986, vol. 135, pp. 93–110.
Molecular Packing and Hydrogen Bonding in the Crystal Structures of the N–(n–Alkyl)–D–gluconamide and the 1–Deoxy–(N–methyl–alkanamido)–D–glucitol Mesogens, Mol. Cryst. Liq. Cryst. 1990, vol. 185, pp. 209–213.
Molecular Crystals and Liquid Crystals, vol. 198 (1991).
Amphiphilic Properties of Synthetic Glycolipids Based on Amide Linkages, Zabel et al., Chemistry and Physics of Lipids, 39 (1986) 313–327.
Liquid–crystalline Behaviour in the N–alkyl Gluconamides and Other Related Carbohydrates, Pfanhemuller, Liquid Crystals, 1986, vol. 1, No. 4, 357–370.
Amphiphilic Properties of Synthetic Glycolipids Based in Amide Linkages, Makromol, Chem. 189, 2433–2442 (1988).
Molecular and Crystal Structures of N–(n–Heptyl)– and N–(n–Decyl)–D–Glyconamide, Fahrnow et al., Carbohydrate Research 176 (1988) 165–174.
Supramolecular Assemblies of Diacetylenic Aldonamides, Frankel et al., J. Am. Chem. Soc., 1991, 113, 7436–7437.
A New Class of Model Glycolipids; Synthesis, Characterization, and Interaction with Lectins, Williams et al., Archives of Biochemistry and Biophysics, vol. 195, No. 1, Jun., pp. 145–151, 1979.
Synthesis of a New Class of Model Glycolipids, Williams et al.—Carbohydrate Research, 67 (1978) C1–C3.
Technical Notes, Scholnick et al. pp. 471–473.
Compositions Comprising Nonionic Glycolipid Surfactants, Filed as U.S. Ser. No. 816,419.
Light Scattering from Nonionic Surfactants of the Sugar–Lipid Hybrid Type in Aqueous Solution, Denkinger et al., J. Phys. Chem., 1989, 93, pp. 1428–1434.
Investigations of a Series of Nonionic Surfactants of Sugar–Lipid Hybrids by Light Scattering and Electron Microscopy, Denkinger et al., Colloid & Polymer Science 268:513 527 (1990).
Monolayers from Synthetic Glycolipids, Emmerling, Polymer Bulletin 6, 305–308 (1982).
Synthesis of New Fluorinated Nonionic Surfactants Derived from Lactose, Ghoul, Journal of Fluorine Chemistry, 59 (1992) 107–112.
Conformational Effects of 1,3,–syn–Diaxial Repulsion and 1,2–gauche Attraction Between Hydroxy Groups in Monomolecular N–Octyl–D–Hexonamide Solutions, Svenson et al., J. Chem. Soc., Perkin Trans 2, 1994, pp. 1023–1028.

*Primary Examiner*—John W. Rollins
*Attorney, Agent, or Firm*—Ronald A. Koatz

[57] ABSTRACT

The present invention relates to a process for producing amido heteroatom containing alkyl aldonamides comprising reacting an amino heteroatom containing alkyl aldonamide and an acid anhydride in water or solvent; heating the mixture and recovering. A second embodiment of the invention relates to a process for making alkoxylated derivatives of heteroatom containing alkyl aldonamide compounds.

34 Claims, No Drawings

U.S. PATENT DOCUMENTS

| | | | |
|---|---|---|---|
| 4,038,294 | 7/1977 | Conner et al. | 554/52 |
| 4,190,429 | 2/1980 | Rutter et al. | 504/159 |
| 4,342,706 | 8/1982 | Conner et al. | 562/85 |
| 4,529,588 | 7/1985 | Smith et al. | 424/70.8 |
| 4,534,964 | 8/1985 | Herstein et al. | 424/70.8 |
| 4,618,675 | 10/1986 | Lichtenthaler | 536/17.2 |
| 4,973,473 | 11/1990 | Schneider et al. | 424/63 |
| 5,037,973 | 8/1991 | Meinetsberger | 536/53 |
| 5,084,270 | 1/1992 | Ciaudelli | 424/59 |

HETEROATOM CONTAINING ALKYL ALDONAMIDE COMPOUNDS AS SUPERIOR FOAMING, MORE SOLUBLE NONIONIC SURFACTANTS AND A PROCESS FOR THEIR MANUFACTURE

This is a Divisional application of Ser. No. 08/351,929, filed Dec. 8, 1994, now abandoned, which is a continuation in part of U.S. Ser. No. 981,644, filed Nov. 25, 1992 which is now abandoned.

TECHNICAL FIELD

The present invention relates to novel heteroatom containing alkyl aldonamide compounds which have improved foam, enhanced water solubility, lower surface tension and favorable critical micelle concentration relative to prior art alkyl aldonamides. More particularly, the invention relates to monosaccharide heteroatom containing alkyl aldonamide compounds comprising at least two heteroatoms in the alkyl chain selected from the group consisting of amine (NH), amine salt (NHA+), ether (O), ester (COO or OOC), amide (NACO, CONA or NCOA) or mixtures thereof; and disaccharide heteroatom containing alkyl aldobionamide compounds comprising at least one heteroatom in the alkyl chain selected from the group consisting of amine (NH), amine salt (NHA+), ether (O), amide (NACO, CONA or NCOA) or mixtures thereof, wherein A is hydrogen (H) or a $C_1$–$C_{18}$ alkyl group that may optionally contain a hydroxyl group.

In addition, the present invention also relates to a new and improved method of manufacture of certain novel alkylamidoalkyl aldonamide compounds.

BACKGROUND OF THE INVENTION

Most surfactants presently used in detergent and personal product compositions are based on, or derived largely from, petrochemicals. Because of increased concern over environmental issues raised by the use, handling and storage of such materials as well as the continually rising costs of such materials, it would be advantageous to develop surfactants which are instead derived from agriculturally grown substances such as carbohydrates. These naturally occurring compounds represent a source of renewable raw materials which are synthetically versatile, inexpensive, aquatically favorable, optically pure and environmentally friendly. In addition, it is most desirable to have surfactants that provide an enhanced copious persistent foam while simultaneously providing an enhanced solubility in water and in aqueous detergent, personal product and oral hygiene compositions. This has become a difficult challenge to meet and it is not surprising to find that considerable resource and effort have been directed towards the discovery and development of new surfactants that provide improved foam and solubility characteristics. The patent literature, cosmetic journals and formularies describe many such compounds, however, they still do not provide all the answers to the problems encountered in making a totally satisfactory surfactant, particularly alkyl aldonamide surfactants. For one thing, it is known that prior art alkyl aldonamides exhibit poor water solubility and little or no foaming performance. While not wishing to be bound by theory, it is believed that the amphiphilic nature of these compounds cause them to pack closely in the solid state through strong amide/hydroxyl hydrogen bonding as well as strong hydrocarbon Van der Waal forces. The net result is an unfavorable heat of hydration, a high Krafft point, low water solubility (precipitation), a poor rate of micellization, an unfavorable surface tension and a poor foaming profile.

It has now been found that the inclusion of a heteroatom in the alkyl chain of an aldonamide compound produces a nonionic surfactant that surprising exhibits a superior water solubility and foaming performance. While not wishing to be bound by theory, it is believed that heteroatom containing alkyl aldonamide compounds pack more loosely (favorably) in the solid state through weaker amide/hydroxyl hydrogen bonding and weaker hydrocarbon Van der Waal forces. The net result is a more favorable heat of hydration, a lower Krafft point, an increased water solubility, an enhanced rate of micellization, a low surface tension and a superior foaming profile.

In addition, it has also been found that the heteroatom containing alkyl aldonamide compounds of the present invention represent a novel, naturally derived, cost-effective, biodegradable, class of nonionic surfactant which have surfactant properties equal to, or better than, other well known petrochemically derived surfactants, thereby indicating that they are viable, environmentally sound alternatives to traditional petrochemical surfactants.

These findings are quite unexpected and have not been recognized or appreciated in the art.

An aldonamide is most generally defined as the amide of an aldonic acid (or aldonolactone) and an aldonic acid, in turn is defined as a sugar substance in which the pseudoaldehyde or pseudoketose group, generally found at the $C_1$ or $C_2$ position on the sugar, has been oxidized to a carboxylic acid group which upon drying cyclizes to an aldonolactone.

Aldonamides may be based on compounds comprising one saccharide unit (e.g., glyceramides, ribonamides, gluconamides or glucoheptonamides), two saccharide units (e.g., lactobionamides, maltobionamides, melibionamides, cellobioamides, gentiobionamides or D-glucopyranosyl-(1–5)-D-arabinonamides) or they may be based on compounds comprising more than two saccharide units (e.g. maltotrionamides or maltohexonamides). Any carbohydrate can be used as long as the sugar has a pseudoaldehyde or pseudoketose group available for oxidation to a carboxylic acid group.

While certain alkyl aldonamides are known in the art, there is no teaching or suggestion of the heteroatom containing alkyl aldonamide compounds of the present invention. In particular, there is no teaching or suggestion of monosaccharide heteroatom containing alkyl aldonamide compounds comprising at least two heteroatoms in the alkyl chain selected from the group consisting of amine (NH), amine salt (NHA+), ether (O), ester (COO or OOC), amide (NACO, CONA or NCOA) or mixtures thereof; and disaccharide heteroatom containing alkyl aldobionamide compounds comprising at least one heteroatom in the alkyl chain selected from the group consisting of amine (NH), amine salt (NHA+), ether (O), amide (NACO, CONA or NCOA) or mixtures thereof, wherein A is hydrogen (H) or a $C_1$–$C_{18}$ alkyl group that may optionally contain a hydroxyl group.

More specifically, there is no teaching or suggestion of a certain novel class of heteroatom containing alkyl aldonamide compound which has improved foam, enhanced water solubility, lower surface tension and favorable critical micelle concentration relative to prior art alkyl aldonamides.

In addition, there is no teaching or suggestion of a new and improved method of manufacture of certain novel heteroatom containing alkyl aldonamide compounds, specifically alkylamidoallcyl aldonamides.

Background

Alkyl Aldonamides

U.S. Pat. No. 2,662,073 to Mehltretter, et al. for example, teaches gluconamide compounds of the formula:

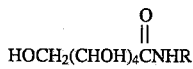

wherein R is an aliphatic hydrocarbon radical having 8 to 18 carbon atoms, a cycloaliphatic radical having 8 to 18 carbon atoms or a rosin radical. The compounds are said to be valuable wetting agents for use in the mercerization of cotton and in the manufacture of viscose yarn. There is clearly no teaching on suggestion of using a heteroatom in the hydrocarbon radical of an alkyl aldonamide compound for improved foam, enhanced water solubility, low surface tension and favorable critical micelle concentration.

U.S. Pat. No. 2,776,951 to Melamed teaches the preparation of vinyloxyethyl gluconamides as polymer precursors. The polymers are said to be useful as wetting agents and as paper, leather or textile finishing agents. There is clearly no teaching or suggestion of using a heteroatom in the hydrocarbon radical of an alkyl aldonamide compound for improved foam, enhanced water solubility, low surface tension and favorable critical micelle concentration.

U.S. Pat. No. 2,721,211 to Buc teaches alkyl formyl phenylene gluconamides as solubilizing agents for vat dye stuffs. The alkyl formyl phenylene radical (R) of these compounds are structurally unrelated to the compounds of the invention which contain a hydrocarbon radical interrupted by a heteroatom. Also, U.S. Pat. No. 4,190,429 to Rutter, et al. teaches adamantyl gluconamides as antimicrobial agents. In both of these patents, there is clearly no teaching or suggestion of using a heteroatom in the hydrocarbon radical of an alkyl aldonamide compound for improved foam, enhanced water solubility, low surface tension and favorable critical micelle concentration.

Fieser, et al. in J. Am. Chem. Soc. 78:2825 (1956) teaches the preparation of a series of N-alkyl arabinonamides and N-alkyl gluconamides for use as an emulsifying agents, where the attached aliphatic radical (R) is from $C_{10}$ to $C_{18}$. The reference teaches that such compounds are poor emulsifying agents and are therefore expected to be poor surfactants with low water solubility and little or no foaming performance. Also, there is clearly no teaching or suggestion that the addition of oxygen or other heteroatoms in the alkyl radical of an alkyl aldonamide compound can enhance the foam and water solubility characteristics of that compound.

Furthermore, the fact that the monosaccharide alkyl aldonamides, where the alkyl group is $C_{10}$ or greater, are poor emulsifiers with low water solubility and little or no foaming performance is also recognized in German Pat. Nos. 2,321,752 and 2,338,087, both to Reiser, et al. (1975).

Specifically, DE 2,321,752 is directed to the preparation of N,N-dialkyl polyhydroxyamide compounds having the formula:

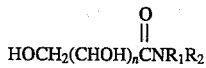

wherein n is 3 to 5; $R_1$ is hydrogen or a linear alkyl group containing 1 to 3 carbon atoms: and $R_2$ is an aliphatic hydrocarbon radical having 4 to 7 carbons in normal or branched arrangement (optionally interrupted by oxygen or sulfur group). The principal patent DE 2,321,752, teaches that alkyl aldonamides having long chained radical (R) groups such as lauryl (12 carbons), cetyl (16 carbons) or stearyl (18 carbons), do not form stable water emulsions. Therefore, it was surprising to find that the heteroatom containing alkyl aldonamide compounds having R groups of 8 carbons or more, provide improved foam, enhanced water solubility, low surface tension and favorable critical micelle concentration. Although, German Pat. Nos. 2,321,752 and 2,338,087, do teach monosaccharide alkyl aldonamide compounds comprising one heteroatom (oxygen or sulfur) in the alkyl chain, and one functional group (hydroxyl) on the alkyl chain, they do not teach or suggest more than one heteroatom (at least two heteroatoms) in an alkyl chain. These references also fail to teach or suggest disaccharide heteroatom containing alkyl aldonamide compounds of the invention comprising at least one heteroatom in the alkyl chain. These compounds are structurally very different. Thus, there is no teaching or suggestion that such alkyl groups when interrupted with, for example, an amine (NH), amine salt (NHA+), ether (O), amide (NCOA) or mixtures thereof, would provide improved foam, enhanced water solubility, low surface tension and favorable critical micelle concentration.

Japanese Patent 1-168653 again recognizes that the monosaccharide aldonamides of the art. (e.g., N-alkyl gluconamides) do not show sufficient emulsifying properties (poor surface-activity). Again, there is a recognition that such compounds are poor emulsifiers and are therefore not expected to provide suitable foam, water solubility, surface tension or critical micelle concentration.

The Japanese patent seeks to address this problem by using N,N-dialkyl polyhydroxyamide compounds where one alkyl group (R) is $C_8$–$C_{18}$ and the other is $C_1$–$C_4$. There is clearly no teaching or suggestion of using a heteroatom in the hydrocarbon radical of an alkyl aldonamide compound for improved foam, enhanced water solubility, low surface tension and favorable critical micelle concentration.

French Patent No. 2,523,962 to Monsigny teaches the compounds:

wherein m is 2 to 6 and $R_3$ is a linear or branched alkyl group containing 6 to 18 carbons. The patent further teaches polyoxyethylene, polyoxypropylene or polyglycerol derivatives of the formula. Again, however, there is no teaching of a hydrocarbon radical (R) when interrupted by a heteroatom, could provide improved foam, enhanced water solubility, low surface tension and favorable critical micelle concentration.

U.S. Pat. No. 4,973,473 to Schneider, et al. and U.S. Pat. No. 5,084,270 to Claudelli teaches skin treatment compositions in which the primary moisturizing agent may be a gluconamide compound. Methyloxypropyl gluconamide is the only example of this ingredient which has the formula:

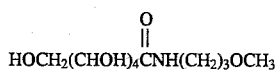

Since this compound is clearly hydrophilic (not surface-active), it cannot be used as a surfactant. There is no suggestion to utilize alkyl chains greater than methyl and there is clearly no teaching or suggestion that alkyl aldonamides with interrupted long alkyl chains containing more than one heteroatom can provide improved foam, enhanced water solubility, low surface tension and favorable critical micelle concentration.

Schneider et al. in Hoppe-Seyler's Z. Physiol. Chem. 330:182 (1963) teaches alkyl gluconyl glycinate compounds having the formula:

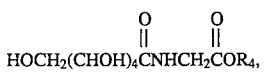
HOCH$_2$(CHOH)$_4$CNHCH$_2$COR$_4$, wherein R$_4$=C$_8$ to C$_{10}$

While this paper does teach monosaccharide aldonamides containing an alkyl group interrupted with an ester functionality, there is no teaching or suggestion that such alkyl groups may be interrupted with, for example, an amine (NH), amine salt (NHA+), ether (O), amide (NCOA) and mixtures thereof, or that the use of such groups would provide improved foam, enhanced water solubility, low surface tension and favorable critical micelle concentration.

Geyer in Chemische Berichte 97:2271 (1964) describes the preparation of N-alkanoyl-N-gluconoyl ethylene diamide compounds having the structure:

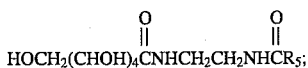
HOCH$_2$(CHOH)$_4$CNHCH$_2$CH$_2$NHCR$_5$;

wherein R$_5$=C$_{15}$, C$_6$; and

Pfannemueller, et al. in Chemistry and Physics of Lipids 37:227 (1985) describes the preparation of N-alkanoyl-N-methyl-N'-gluconoyl ethylene diamide compounds of the formula:

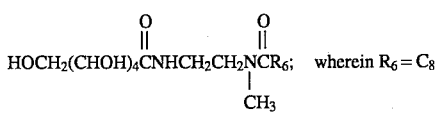
HOCH$_2$(CHOH)$_4$CNHCH$_2$CH$_2$NCR$_6$;  wherein R$_6$ = C$_8$
                                     |
                                    CH$_3$ These references teach monosaccharide aldonamides containing an alkyl group that is interrupted with an amide (NACO) group wherein A is H or CH$_3$. The reference fails to teach heteroatom containing alkyl aldonamide compounds wherein the heteroatom is an amine (NH), amine salt (NHA+), ether (O), amide (NCOA) [which is structurally different than NACO] or mixtures thereof, wherein A is hydrogen (H) or a C$_1$–C$_{18}$ alkyl group that may optionally contain a hydroxyl group. The reference also fails to teach monosaccharide alkyl aldonamide compounds comprising at least two heteroatoms in the alkyl chain. Again, there is no teaching or suggestion of alkyl aldonamides with such interrupting groups provide greater foam, enhanced water solubility, lower surface tension and favorable critical micelle concentration relative to their counterparts containing no heteroatoms in the alkyl chain. Furthermore, there is clearly no teaching or suggestion of sugar compounds having two saccharide units or greater (e.g., lactobionamides, maltobionamides, maltotrionamides etc.), together within an interrupted alkyl group [e.g. amine (NH), amine salt (NHA+), ether (O), amide (NCOA) or mixtures thereof], can provide improved foam, enhanced water solubility, low surface tension and favorable critical micelle concentration.

In terms of processing, Geyer describes a method for identifying the structure of 1,2-bis-D-gluconoylamidoethane, 1,6-bis-D-gluconoylamidohexane and 1-amino-2-D-gluconoylamidoethane. The method involves polyacetylating the above compounds with acetic acid and pyridine at room temperature to 60° C., for 6 to 24 hours. The reaction is then poured onto ice water and recrystallized or extracted with an organic solvent. Differences in the IR structure of the polyacetylated compounds were used to determine the structure of the parent compounds. Also, Geyer describes of method for preparing 1-acetamido-2-D-gluconoylamidoethane which involves reacting 1-amino-2-D-gluconoylamidoethane with acetic anhydride in methanol at room temperature for certain period of time. The product was allowed to crystallize out of solution, and subsequently recrystallized from hot methanol sprayed with ether in about 34% isolated yield. In addition, N-[β-D-gluconoylamidoethyl]-phthalic acid monoamide (65% isolated yield) and N-[β-D-gluconoylamidoethyl]-maleic acid monoamide (72% isolated yield) were also prepared in an similar manner.

Pfannemuller et al. describes a method for preparing N-octanoyl-N'glyconoylethylenediamide and N-octanoyl-N-methyl-N'-glyconoylethylenediamide which involves reacting N'-gluconoylethylenediamine and N-methyl-N'-gluconoylethylenediamine with a mixed anhydride in ethylene glycol at room temperature. The mixed anhydride is prepared separately by reacting octanoic acid with ethyl chloroformate in diethylether and pyridine. The resulting by-product (pyridinium chloride) is subsequently filtered and washed with ether followed by the addition of the mixed anhydride to the reaction mixture. The entire contents of the flask was allowed to stand overnight at 4° C. and the resulting percipitate was filtered, rinsed with methanol, then ether, and dried under vacuum giving an isolated yield of about 48% to 52%.

In light of the potentially large demand for heteroatom containing alkyl aldonamides for use in detergent, personal product and oral hygiene compositions, there is clearly no teaching or suggestion of an new and improved method of manufacture of heteroatom containing alkyl aldonamide compounds of the invention. Prior art processes discussed above, result in the formation of several non-surfactant aldonamides in low yield and often require costly, non-commercial methods of manufacture. Therefore it is desirable to provide an improved, novel, viable, cost-effective, commercially feasible process for the manufacture of nonionic heteroatom containing alkyl aldonamide surfactants, particularly alkylamidoalkyl aldonamide surfactants. These surfactants are especially well suited for the manufacture of clear, colorless, high sudsing detergent compositions which often require an inexpensive source of sugar-based surfactant. In addition, modern detergent compositions which often employ bleaching agents which generate hydrogen peroxide, that could potentially oxidize amino containing alkyl aldonamides to undesirable by-products. Therefore, the process of the invention not only provides a method for amidating the amino group of a heteroatom containing alkyl aldonamide, but it also provides an improved class of alkylamidoalkyl aldonamide compound that is especially suited for detergent applications which is no longer susceptible to the possible formation of oxidized amino color bodies, nitrosamines, hydroxylamines, odor and the like.

U.S. Pat. No. 5,037,973 to Meinetsbeger teaches a series of bis-alkyl aldonamide compounds as intermediates for pharmacological applications. While this paper does teach bis-alkyl aldonamide compounds containing heteroatoms, there is no teaching or suggestion that the use of such radicals would provide improved foam, enhanced water solubility, low surface tension and favorable critical micelle concentration. In addition, the heteroatom containing alkyl aldonamides of this invention are monomeric in nature (structurally very different) whereas the bis-alkyl aldonamide compounds of U.S. Pat. No. 5,037,973 are dimeric in nature (too hydrophilic, unbalanced) and would not be considered useful as surfactants for improved foam, enhanced water solubility, low surface tension and favorable critical micelle concentration.

U.S. Pat. Nos. 3,766,367 and 3,855,290 to Zak, et al. as well as U.S. Pat. Nos. 4,038,294 and 4,342,706 to Conner, et al. teach quaternary halide gluconamide compounds of the formulas;

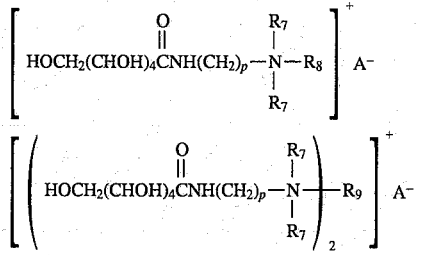

wherein:
$R_7 = C_1-C_2$, $CH_2CH_2OH$

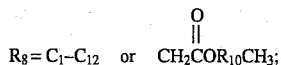

$R_9 = C_2-C_6$;
p=2–4;
A–=Cl—, Br— or $R_{11}C_6H_4SO_3$—
q=1–3;
$R_{10} = C_7-C_{21}$;
$R_{11} = H$, $CH_3$;

These compounds are said to be useful as emollients which are substantive to skin or hair and are further taught in U.S. Pat. Nos. 3,990,991 to Gerstein, 4,534,964 to Herstein et al. and 4,529,588 to Smith et al. which all describe conditioning shampoo compositions comprising quaternary halide gluconamide compounds. There is clearly no teaching or suggestion in any of these references, of using heteroatom containing alkyl aldonamide compounds of the invention for improved foam, enhanced water solubility, low surface tension and favorable critical micelle concentration. Also the heteroatom containing alkyl aldonamide compounds of the present invention are structurally very different and do not contain a quaternary ammonium functional group which is responsible for the emolliency and conditioning effect.

Finally, there are several references teaching the molecular and liquid crystal structure of alkyl aldonamides, see for example. J. Am. Chem. Soc. 109(11):3387 (1987), 110:2861 (1988) and 112:1768 (1990) to Fuhrhop, et al.; Mol. Cryst. Liq. Cryst. I35:93 (1986) to Baeyens-Volant, et al., 185:209 (1990) to Jeffery and 198:381 (1991) to Van Doren. et al.; Chemistry and Physics of Lipids 39:313 (1986) to Zabel. et al.; Liquid Crystals 1(4):357 (1986) and Makrolmol. Chem. 189:2433 (1988) to Pfannemueller, et al.; Carbohydrate Research 176:165 (1988) to Fahrnow, et al. and J. Am Chem. Soc. 113:7436 (1991) to Frankel, et al. There is clearly no teaching or suggestion in any of these references, of using a heteroatom in the hydrocarbon radical of an alkyl aldonamide compound for improved foam, enhanced water solubility, low surface tension and favorable critical micelle concentration.

Alkyl Aldobionamides

U.S. Pat. Nos. 2,752,334 to Walton and 2,785,152 to Jones teach aldobionamide compounds prepared by the reaction of aldobionic acids or aldobionolactones with fatty amines or fatty amino acid esters. The compounds are said to be useful as an emulsifier in food compositions and as antimycotic agents. There is no teaching or suggestion that the use of a heteroatom [e.g., amine (NH), amine salt (NHA+), ether (O), amide (NACO, CONA or NCOA) or mixtures thereoff in the aliphatic hydrocarbon radical of an alkyl aldobionamide compound can improve foam, enhance water solubility, lower surface tension and provide a favorable critical micelle concentration.

Williams, et al. in Archives of Biochem. and Biophysics. 195(1):145 (1979) and Carbohydrate Research 67:C1–C3 (1978) teach aldobionamide compounds prepared by the reaction of aldobionic acids with alkyl amines. Again, there is no teaching or suggestion that the alkyl group of the alkyl amine may contain a heteroatom, nor is there any teaching or suggestion of using a heteroatom in the alkyl radical of an aldobionamide compound for improved foam, enhanced water solubility, low surface tension and favorable critical micelle concentration.

Scholnick, et al. in J. Dairy Sci. 63(3):471 (1980) teach aldobionamide compounds as effective chelating agents of ferric ion. There is clearly no teaching or suggestion of using a heteroatom in the alkyl radical of an aldobionamide compound for improved foam, enhanced water solubility, low surface tension and favorable critical micelle concentration.

In copending U.S. Ser. No. 816,419, the assignee of the subject application has filed an application directed to the use of the broad class of aldonamide surfactants in detergent or personal product compositions. The application, U.S. Ser. No. 981,644, has been filed as a separate application on the same date as U.S. Ser. No. 816,419. These applications have a few examples of using a heteroatom (i.e., ether and ester in the aliphatic hydrocarbon), however there is no teaching or suggestion that this heteroatom is responsible for improved foam, enhanced water solubility, low surface tension and favorable critical micelle concentration. Also, U.S. Ser. No. 981,644 has been filed as world application WO 94/12511. In any event. U.S. Ser. No. 816,419 is not available as a reference since it is filed on the same date as U.S. Ser. No. 981,644.

Finally, there are several references teaching the molecular and micellar structure of alkyl aldobionamides generally, but are otherwise unrelated to the compounds of the invention, see for example, J. Phys. Chem. 93(4):1482 (1989) and Colloid Poylm. Sci. 268(6):513 (1990) to Denkinger, et al. and Polym. Bull. (Berlin) 6(5–6):305 (1982) to Emmerling.

There is clearly no teaching or suggestion in any of these references, of using a heteroatom in the hydrocarbon radical of an alkyl aldonamide compound for improved foam, enhanced water solubility, low surface tension and favorable critical micelle concentration.

Since most detergent and personal product compositions are based on petrochemical ingredients, it would be most desirable to use materials which are instead naturally derived, such as carbohydrates. These renewable raw materials have the distinct advantage of being readily available, inexpensive, biodegradable, aquatically favorable and optically pure.

Thus the ability to find a naturally derived, environmentally friendly compound, that simultaneously provides an enhanced copious persistent foam and enhanced water solubility as well as a low surface tension and favorable critical micelle concentration is a significant achievement.

Accordingly, it is an object of the present invention to provide novel heteroatom containing alkyl aldonamide compounds as nonionic surface-active agents for detergent, personal product, oral hygiene, food and pharmacological applications.

It is another object of the present invention to provide several novel naturally derived, cost-effective, biodegradable nonionic heteroatom containing alkyl aldonamide surfactants.

It is another object of the present invention to provide an improved class of aldonamide surfactant that exhibits an enhanced copious persistent foam and increased water solubility.

It is still another object of the present invention to provide a class of aldonamide surfactant which does not become turbid or produce sedimentation upon standing in water or in aqueous detergent, personal product and oral hygiene compositions.

It is still another object of the present invention to provide nonionic heteroatom containing alkyl aldonamide surfactants that have low surface tension and a favorable critical micelle concentration.

It is still another object of the present invention to provide an improved class of heteroatom containing alkyl aldonamide compound that is no longer susceptible to the possible formation of oxidized amino color bodies, nitrosamines, hydroxylamines, odor and the like.

It is still another object of the present invention to provide an improved, novel, viable, cost-effective, commercially feasible process for the manufacture of nonionic heteroatom containing alkyl aldonamide surfactants, particularly alkylamidoalkyl aldonamide surfactants.

It is a final object of the present invention to prepare solid nonionic heteroatom containing alkyl aldonamide surfactants in good yield, high purity, and desirable color without hydroxyl group protection, oligomerization or polymerization. These and other objects will become readily apparent from the detailed description which follows.

SUMMARY OF THE INVENTION

The present invention relates to novel heteroatom containing alkyl aldonamide compounds which have improved foam, enhanced water solubility, lower surface tension and favorable critical micelle concentration relative to prior art alkyl aldonamides. More particularly, the invention relates to monosaccharide heteroatom containing alkyl aldonamide compounds comprising at least two heteroatoms in the alkyl chain selected from the group consisting of amine (NH), amine salt (NHA+), ether (O), ester (COO or OOC), amide (NACO, CONA or NCOA) or mixtures thereof; and disaccharide heteroatom containing alkyl aldobionamide compounds comprising at least one heteroatom in the alkyl chain selected from the group consisting of amine (NH), amine salt (NHA+), ether (O), amide (NACO, CONA or NCOA) or mixtures thereof, wherein A is hydrogen (H) or a $C_1$–$C_{18}$ is alkyl group that may optionally contain a hydroxyl group.

While wishing not to be bound by theory, the present invention is based on the discovery that heteroatom containing alkyl aldonamide compounds are believed to pack more loosely (favorably) in the solid state through weaker amide/hydroxyl hydrogen bonding and hydrocarbon Van der Waal forces. The net result is a more favorable heat of hydration, a lower Krafft point, an increased water solubility, an enhanced rate of micellization, a low surface tension and a superior foaming profile.

In addition, it has also been found that the heteroatom containing alkyl aldonamide compounds of the present invention represent a novel, naturally derived, cost-effective, biodegradable, class of nonionic surfactant which have surfactant properties equal to, or better than, other well known petrochemically derived surfactants, thereby indicating that they are viable, environmentally sound alternatives to traditional petrochemical surfactants.

Finally, a new and improved method of manufacture of certain novel alkylamidoalkyl aldonamides has been found. The improvement comprises reacting an alkylaminoalkyl aldonamide with an alkyl anhydride in water or an organic solvent at elevated temperatures in the presence or absence of an organic or inorganic base followed by treatment with a bleaching or reducing agent. These and other objects will become readily apparent from the detailed description which follows.

DETAILED DESCRIPTION OF THE INVENTION

The present invention relates to a novel class of environmentally friendly "green" nonionic surfactant. In particular, the invention relates to heteroatom containing alkyl aldonamide compounds which have improved foam, enhanced water solubility, lower surface tension and favorable critical micelle concentration relative to prior art alkyl aldonamide compounds which do not comprise a heteroatom in the alkyl chain.

More specifically, the first embodiment of the invention relates to monosaccharide heteroatom containing alkyl aldonamide compounds comprising at least two heteroatoms in the alkyl chain selected from the group consisting of amine (NH), amine salt (NHA+), ether (O), ester (COO or OOC), amide (NACO, CONA or NCOA) or mixtures thereof; and the second embodiment of the invention relates to disaccharide heteroatom containing alkyl aldobionamide compounds comprising at least one heteroatom in the alkyl chain selected from the group consisting of amine (NH), amine salt (NHA+), ether (O), amide (NACO, CONA or NCOA) or mixtures thereof, wherein A is hydrogen (H) or a $C_1$–$C_{18}$ alkyl group that may optionally contain a hydroxyl group.

The third embodiment of the invention relates to a novel, viable, cost-effective, commercially feasible process for the manufacture of nonionic heteroatom containing alkyl aldonamide surfactants, particularly alkylamidoalkyl aldonamide, alkyloxyalkylamidoalkyl aldonamide surfactants and the like, wherein the amide group is represented by NCOA. The process is an improvement over prior art known processes for the preparation of N-alkanoyl-N-gluconoyl-ethylene diamiae compounds and N-alkanoyl-N-methyl-N'-gluconoylethylene diamide compounds, wherein the improvement comprises reacting an alkylaminoalkyl aldonamide with an alkyl anhydride in water or an organic solvent at elevated temperatures in the presence or absence of an organic or inorganic base followed by treatment with a bleaching or reducing agent.

The third embodiment of the invention is particularly directed to preparing solid alkylamidoalkyl aldonamides in good yield, high purity, and desirable color without hydroxyl group protection, oligomerization or polymerization.

Furthermore the third embodiment of the invention is also particularly directed to preparing an improved class of heteroatom containing alkyl aldonamide compound that is no longer susceptible to the possible formation of oxidized amino color bodies, nitrosamines, hydroxylamines, odor and the like.

An aldonamide is most generally defined as the amide of an aldonic acid (or aldonolactone) and an aldonic acid, in turn is defined as a sugar substance in which the pseudoaldehyde or pseudoketose group, generally found at the $C_1$ or $C_2$ position on the sugar, has been oxidized to a carboxylic acid group which upon drying cyclizes to an aldonolactone. Aldonamides may be based on compounds comprising one saccharide unit (e.g., glyceramides, ribonamides, gluconamides or glucoheptonamides), two saccharide units (e.g., lactobionamides, maltobionamides, melibionamides, cellobioamides, gentiobionamides or D-glucopyranosyl-(1-5)-D-arabinonamides) or they may be based on compounds comprising more than two saccharide units (e.g. maltotrionamides or maltohexonamides). Any carbohydrate can be used as long as the sugar has a pseudoaldehyde or pseudoketose group available for oxidation to a carboxylic acid group.

The heteroatom containing alkyl aldonamide compounds are most generally defined by the formula:

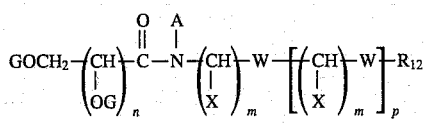

wherein:
n=1–6;
m=1–6;
X=H, a $C_1$–$C_4$ alkyl group or mixtures; thereof;
W=amine (NH), amine salt (NHA+), ether (O), sulfur (S), sulfur monoxide (SO), sulfur dioxide ($SO_2$), ester (COO or OOC), amide (NACO, CONA or NCOA) group or mixtures thereof;
p=0–50;
G=H, a mono-, di-, oligo-, polysaccharide group, a $(CH_2CH_2O)_q$—H, $(CH_2CHCH_3O)_r$—H group or mixtures thereof;
q=1–50;
r=1–50;
A=H, a hydroxy $C_1$–$C_{18}$ alkyl group, a $C_1$–$C_{18}$ straight or branched chain, saturated or unsaturated hydrocarbon which may be unsubstituted or substituted with an aromatic, cycloaliphatic, mixed aromatic aliphatic radical or mixtures thereof; and $R_{12}$ is a straight or branched chain, saturated or unsaturated hydrocarbon which may be unsubstituted or substituted with an aromatic, cycloaliphatic, or mixed aromatic aliphatic radical comprising from about 4 to about 28 carbon atoms.

A monosaccharide heteroatom containing alkyl aldonamide compound which preferably comprises at least two heteroatoms in the alkyl chain is more specifically defined by the formula:

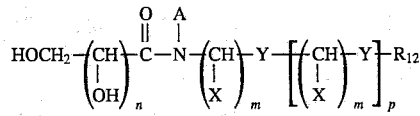

wherein:
n=1–5;
m=1–5;
X=H, a $C_1$–$C_2$ alkyl group or mixtures thereof;
Y=amine (NH), amine salt (NHA+), ether (O), ester (COO or OOC), amide (NAC, O, CONA or NCOA) group or mixtures thereof;
p=1–5;
A=H, a hydroxy $C_1$–$C_{10}$ alkyl group, a $C_1$–$C_{10}$ straight or branched chain, saturated or unsaturated hydrocarbon group or mixtures thereof; and $R_{12}$ is a straight or branched chain, saturated or unsaturated hydrocarbon which may be unsubstituted or substituted with an aromatic, cycloaliphatic, or mixed aromatic aliphatic radical comprising from about 6 to about 24 carbon atoms.

More preferably:
n=2–5;
m=1–4;
X=H, a $C_1$ alkyl group or mixtures thereof;
Y=amine (NH), amine salt (NHA+), ether (O), ester (COO or OOC), amide (NACO, CONA or NCOA) group or mixtures thereof;
p=1–4;
A=hydrogen (H) or a $C_1$–$C_8$ alkyl group that optionally may contain a hydroxyl group; and $R_{12}$ is a straight or branched chain, saturated or unsaturated hydrocarbon comprising from about 8 to about 22 carbon atoms.

Most preferably:
n=3–5;
m=1–3;
X=H, a $C_1$ alkyl group or mixtures thereof;
Y=amine (NH), amine salt (NHA+), ether (O), ester (COO or OOC), amide (NCOA) group or mixtures thereof;
p=1–3;
A=hydrogen (H) or a $C_1$–$C_6$ alkyl group that optionally may contain a hydroxyl group; and $R_{12}$ is a straight or branched chain, saturated or unsaturated hydrocarbon comprising from about 11 to about 22 carbon atoms.

A disaccharide heteroatom containing alkyl aldobionamide compound which preferably comprises at least one heteroatom in the alkyl chain is more specifically defined by the formula:

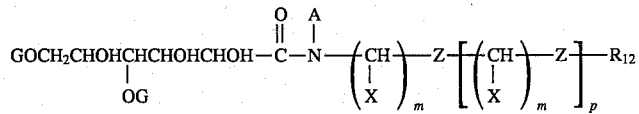

wherein:
m=1–5;
X=H, a $C_1$–$C_2$ alkyl group or mixtures thereof;
Z=amine (NH), amine salt (NHA+), ether (O), amide (NACO, CONA or NCOA) group or mixtures thereof;
p'=0–5;
G=H, a monosaccharide or mixtures thereof;

A=H, a hydroxy $C_1$–$C_{10}$ alkyl group, a $C_1$–$C_{10}$ straight or branched chain, saturated or unsaturated hydrocarbon group or mixtures thereof; and $R_{12}$ is a straight or branched chain, saturated or unsaturated hydrocarbon which may be unsubstituted or substituted with an aromatic, cycloaliphatic, or mixed aromatic aliphatic radical comprising from about 4 to about 28 carbon atoms.

More preferably:
m=1–4;
X=H, a $C_1$ alkyl group or mixtures thereof;
Z=amine (NH), amine salt (NHA+), ether (O), amide (NACO, CONA or NCOA) group or mixtures thereof;
p'=0–4;
G=H, a monosaccharide or mixtures thereof;
A=hydrogen (H) or a $C_1$–$C_8$ alkyl group that optionally may contain a hydroxyl group; and $R_{12}$ is a straight or branched chain, saturated or unsaturated hydrocarbon comprising from about 6 to about 24 carbon atoms.

Most preferably:
m=1–3;
X=H, a $C_1$ alkyl group or mixtures thereof;
Z=amine (NH), amine salt (NHA+), ether (O), amide (NCOA) group or mixtures thereof;
p'=1–3;
G=H, a monosaccharide or mixtures thereof;
A=hydrogen (H) or a $C_1$–$C_6$ alkyl group that optionally may contain a hydroxyl group; and $R_{12}$ is a straight or branched chain, saturated or unsaturated hydrocarbon comprising from about 8 to about 22 carbon atoms.

A specific example of a monosaccharide heteroatom containing alkyl aldonamide compound of the invention is $C_8/C_{10}$ oxypropyl D-gluconamide having the formula:

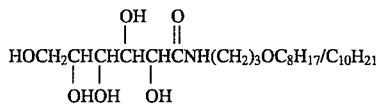

wherein:
n=4;
m=3;
X=hydrogen (H);
Y=oxygen (O);
p=0;
A=hydrogen; and
$R_{12}$=$C_6H_{13}$ (1%), $C_8H_{17}$ (59%), $C_{10}H_{21}$ (39%), $C_{12}H_{25}$ (1%).

Another specific example of a monosaccharide heteroatom containing alkyl aldonamide compound of the invention is $C_{12}$–$C_{15}$ oxypropylaminopropyl D-glucoheptonamide having the formula:

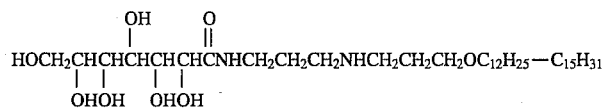

wherein:
n=5;
m=3;
X=hydrogen (H);
Y=oxygen (O) or nitrogen (NH);
p=1;
A=hydrogen; and
$R_{12}$=$C_{12}H_{25}$ (25%), $C_{13}H_{27}$ (39%), $C_{14}H_{29}$ (21%), $C_{15}H_{31}$(15%).

Yet another specific example of a monosaccharide heteroatom containing alkyl aldonamide compound of the invention is $C_{12}$–$C_{15}$ oxypropylaminopropyl D-gluconamide hydrochloride having the formula:

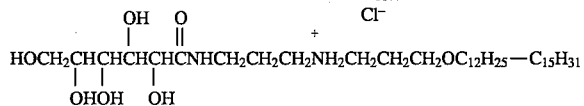

wherein:
n=4;
m=3;
X=hydrogen (H);
Y=oxygen (O) or nitrogen ($NH_2$+);
p=1;
A=hydrogen; and
$R_{12}$=$C_{12}H_{25}$(25%), $C_{13}H_{27}$(39%), $C_{14}H_{29}$(21%), $C_{15}H_{31}$(15%).

Yet another specific example of a monosaccharide heteroatom containing alkyl aldonamide compound of the invention is $C_{12}$–$C_{15}$ oxypropylacetamidopropyl D-gluconamide having the formula:

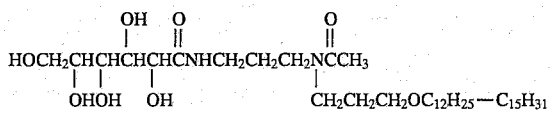

wherein:
n=4;
m=3;
X=hydrogen (H);
Y=oxygen (O) or nitrogen (NCOA);
p=1;
A=hydrogen or CH₃; and
$R_{12}=C_{12}H_{25}(25\%)$, $C_{13}H_{27}(39\%)$, $C_{14}H_{29}$ (21%), $C_{15}H_{31}$ (15%).

Yet another specific example of a monosaccharide heteroatom containing alkyl aldonamide compound of the invention is N-gluconyl dodecyldi(oxyethyl) glycinate, also known as N-gluconyl dodecyl(diethylene glycol) ether glycinate, N-gluconyl (diethylene glycol) monododecyl ether glycinate and as N-gluconyl dodecyl(dioxyethylene) glycinate having the formula:

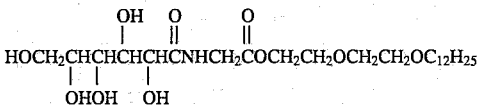

wherein:
n=4;
m=1 or 2;
X=hydrogen (H);
Y=ester (COO) or oxygen (O);
p=2;
G=hydrogen;
A=hydrogen; and
$R_{12}=C_{12}H_{25}$.

A specific example of a disaccharide 2heteroatom containing alkyl aldonamide compound of the invention is dodecyloxypropyl D-lactobionamide having the formula:

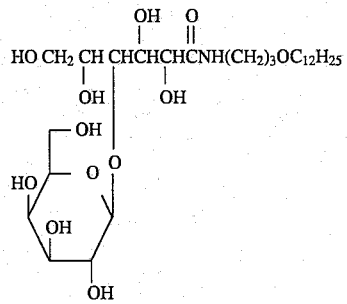

wherein:
m=3;
X=hydrogen:
Z=oxygen (O);
p'=0:
G=hydrogen or galactose:
A=hydrogen; and
$R_{12}=C_{12}H_{25}$.

Another specific example of a disaccharide heteroatom containing alkyl aldonamide compound of the invention is $C_{12}$–$C_{15}$ oxypropylaminopropyl D-lactobionamide hydrochloride having the formula:

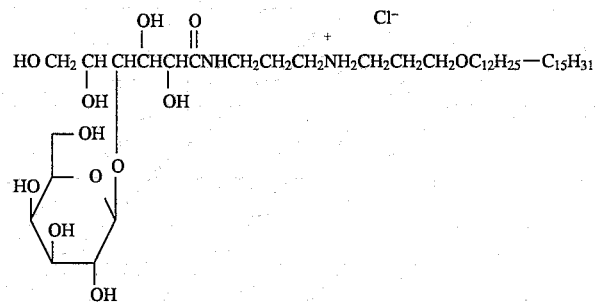

wherein:
m=3;
X=hydrogen (H);
Z=oxygen (O) or nitrogen (NH₂+);
p'=1;
G=hydrogen or galactose;
A=hydrogen; and
$R_{12}=C_{12}H_{25}(25\%)$, $C_{13}H_{27}(39\%)$, $C_{14}H_{29}(21\%)$, $C_{15}H_{31}(15\%)$.

Yet another specific example of a disaccharide heteroatom containing alkyl aldonamide compound of the invention is $C_{12}$–$C_{15}$ oxypropylacetamidopropyl D-maltobionamide having the formula:

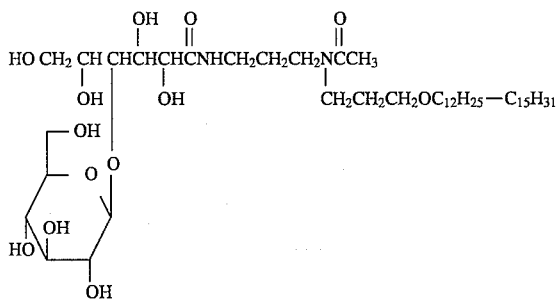

wherein:
m=3;
X=hydrogen (H);
Z=oxygen (O) or nitrogen (NCOA);
p'=1;
G=hydrogen or glucose;
A=hydrogen or $CH_3$; and
$R_{12}=C_{12}H_{25}(25\%)$, $C_{13}H_{27}(39\%)$, $C_{14}H_{29}(21\%)$, $C_{15}H_{31}(15\%)$.

Yet another specific example of a disaccharide heteroatom containing alkyl aldonamide compound of the invention is dodecyltri(oxyethyl)oxy propyl D-glucopyranosyl-(1–5)-D-arabinonamide, also known as dodecyl (triethylene glycol)propylene glycol ether D-glucopyranosyl-(1–5)-D-arabinonamide, (triethylene glycol)propylene glycol monododecyl ether D-glucopyranosyl-(1–5)-D-arabinonamide and as dodecyl(trioxyethylene)oxypropylene D-glucopyranosyl-(1–5)-D-arabinonamide having the formula:

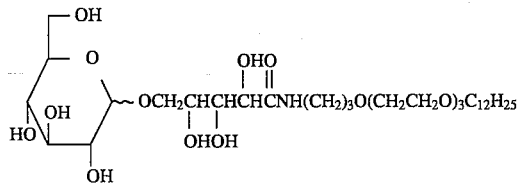

wherein:
m=3 or 2;
X=hydrogen;
Z=oxygen (O);
p'=3;
G=hydrogen or glucose;
A=hydrogen; and
$R_{12}=C_{12}H_{25}$.

D-Glucopyranosyl-(1–5)-D-arabinonic acid and its lactone are readily prepared from isomaltulose (also known as palatinose) by aqueous alkaline oxidation with oxygen or air [see DE-OS 3,248,404 (1982), EP 114,954 (1983), U.S. Pat. No. 4,618,715 (1986) and Chem. Abstr. 102, 7034x (1985) to Lichtenthaler et al.], and isomaltulose is obtained commercially by biochemical dehydrogenation of sucrose with *Agrobacterium tumefaciens* [see *Zuckerind.* 115:20 (1990) to Buchholz et al.].

Other examples of compounds of the invention are set forth below:
alkyloxymethyl D-gluconamide
alkyloxyethyl D-gluconamide
alkyloxybutyl D-gluconamide
alkyloxypentyl D-gluconamide
alkyloxyethyloxymethyl D-gluconamide
alkyldi(oxyethyl)oxymethyl D-gluconamide
alkyldi(oxyethyl) D-gluconamide
alkyltri(oxyethyl) D-gluconamide
alkyltetra(oxyethyl) D-gluconamide
alkylpenta(oxyethyl) D-gluconamide
alkylhexa(oxyethyl) D-gluconamide
alkylhepta(oxyethyl) D-gluconamide
alkylocta(oxyethyl) D-gluconamide
alkyldi(oxypropyl)oxyethyl D-gluconamide
alkyltri(oxypropyl)oxyethyl D-gluconamide
alkylocta(oxypropyl)oxyethyl D-gluconamide
alkyldi(oxyethyl)oxypropyl D-gluconamide
alkyltri(oxyethyl)oxypropyl D-gluconamide
alkyltetra(oxyethyl)oxypropyl D-gluconamide
alkylpenta(oxyethyl)oxypropyl D-gluconamide
alkylhexa(oxyethyl)oxypropyl D-gluconamide
alkylhepta(oxyethyl)oxypropyl D-gluconamide
alkylocta(oxyethyl)oxypropyl D-gluconamide
alkyloxymethyl D-lactobionamide
alkyloxyethyl D-lactobionamide
alkyloxybutyl D-lactobionamide
alkyloxypentyl D-lactobionamide
alkyl(oxyethyl)oxymethyl D-lactobionamide
alkyldi(oxyethyl)oxymethyl D-lactobionamide
alkyldi(oxyethyl) D-lactobionamide
alkyltri(oxyethyl) D-lactobionamide
alkyltetra(oxyethyl) D-lactobionamide
alkylpenta(oxyethyl) D-lactobionamide
alkylhexa(oxyethyl) D-lactobionamide
alkylhepta(oxyethyl) D-lactobionamide
alkylocta(oxyethyl) D-lactobionamide
alkyldi(oxypropyl)oxyethyl D-lactobionamide
alkyltri(oxypropyl)oxyethyl D-lactobionamide
alkylocta(oxypropyl)oxyethyl D-lactobionamide
alkyldioxyethyl)oxypropyl D-lactobionamide
alkyltri(oxyethyl)oxypropyl D-lactobionamide
alkyltetra(oxyethyl)oxypropyl D-lactobionamide
alkylpenta(oxyethyl)oxypropyl D-lactobionamide
alkylhexa(oxyethyl)oxypropyl D-lactobionamide
alkylhepta(oxyethyl)oxypropyl D-lactobionamide
alkyloeta(oxyethyl)oxypropyl D-laetobionamide
alkyloxyethyl D-maltobionamide
alkyloxyethyloxymethyl D-maltobionamide
alkylhexa(oxyethyl) D-maltobionamide
alkyloxyethyl D-glueoheptonamide
alkyloxyethyl D-melibionamide
alkyloxyethyl D-cellobionamide
alkyloxyethyl D-gentiobionamide
alkyloxyethyl D-glucopyranosyl-(1–5)-D-arabinonamide
N-gluconyl alkyl(oxyethyl)glycinate
N-gluconyl alkyltri(oxyethyl)glycinate
N-gluconyl alkyltetra(oxyethyl)glycinate
N-gluconyl alkyltri(oxyethyl) N-methylglycinate
N-gluconyl dialkyldi(oxyethyl) aspartate
N-gluconyl alkyldi(oxyethyl) alaninate
N-gluconyl allcyltetra(oxyethyl) β-alaninate
N-gluconyl alkyldi(oxypropyl) N-methylalaninate N-gluconyl alkyltri(oxyethyl) α-aminobutyrate
N-gluconyl alkyl(oxyethyl)sareosinate
N-gluconyl alkyldi(oxyethyl)sarcosinate
N-gluconyl alkyltri(oxyethyl) sarcosinate
N-gluconyl altcyltri(oxyethyl)leucinate
N-lactobionyl alkyldi(oxyethyl)glycinate
N-lactobionyl alkyltri(oxyethyl) alaninate
N-lactobionyl alkyltetra(oxyethyl) β-alaninate
N-lactobionyl alkyldi(oxyethyl) N-methylalaninate
N-lactobionyl alkyltri(oxyethyl) α-aminobutyrate
N-lactobionyl alkyltri(oxyethyl) α-aminoisobutyrate
N-lactobionyl alkyltri(oxyethyl) ε-aminocarproate
N-lactobionyl alkyldi(oxyethyl) sarcosinate
N-lactobionyl alkyltri(oxyethyl)leucinate
N-glucoheptonyl alkyl(oxyethyl)glycinate trioxyethylene ether
N-maltobionyl alkyl(oxyethyl) glyeinate tetraoxyethylene ether
N-cellobionyl alkyl(oxyethyl) glycinate
alkyloxypropyl D-gluconamide monooxyethylene ether
alkyloxypropyl D-gluconamide dioxyethylene ether
alkyloxypropyl D-gluconamide trioxyethylene ether
alkyloxypropyl D-gluconamlde tetraoxyethylene ether
alkyloxypropyl D-gluconamide pentaoxyene(hylene ether
alkyloxypropyl D-gluconamide hexaoxyethylene ether
alkyloxypropyl D-gluconamide heptaoxyethylene ether
alkyloxypropyl D-gluconamide octaoxyethylene ether
alkyloxypropyl D-gluconamide nonaoxyethylene ether
alkyloxypropyl D-gluconamide decaoxyethylene ether
alkyloxypropyl D-gluconamide trioxypropylene ether
alkyloxyethyl D-gluconamide dioxyethylenetrioxypropylene ether
alkyloxyethyl D-gluconamide trioxypropylenedioxyethylene ether
alkyloxypropyl D-lactobionamide monooxyethylene ether
alkyloxypropyl D-lactobionamide dioxyethylene ether
alkyloxypropyl D-lactobionamide trioxyethylene ether
alkyloxypropyl D-lactobionamide tetraoxyethylene ether
alkyloxypropyl D-maltobionamide dioxyethylene ether
alkyloxypropyl D-maltobionamide pentaoxypropylene ether
alkyloxypropyl D-maltobionamide decaoxypropylene ether
alkylamidopropyl D-lactobionamide hexaoxyethylene ether Wherein the alkyl group contains from about 4 to about 28 carbon atoms, preferably from about 6 to about 24 carbon atoms and even more preferably from about 8 to about 22 carbon atoms.

The A group is most preferably hydrogen or a $C_1$ to $C_6$ alkyl group that optionally may contain a hydroxyl group, however it may also be a hydroxy $C_1$ to $C_{18}$ alkyl group or a $C_1$ to $C_{18}$ straight or branched chain, saturated or unsaturated hydrocarbon radical. The A group may also be interrupted by a heteroatom and may have the same structure as the group attached to the nitrogen atom.

If the A or $R_{12}$ group is an aliphatic radical, suitable examples include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, coco, soya, tallow, tall oil, castor, corp, cottonseed, palm, rapeseed, safflower, sesame, sunflower, fish oil, allyl, octenyl, nonenyl, decenyl, undecenyl, dodecenyl, tridecenyl, tetradecenyl, pentadecenyl, hexadecenyl, heptadecenyl, octadecenyl (oleyl), linoleyl and linolenyl.

If the A or $R_{12}$ group is interrupteel by an aromatic radical, the aromatic group may be for example, benzyl or aniline. Cycloaliphatic radicals are exemplified but are not limited to cyclopentyl and cyclohexyl. Suitable mixed aromatic aliphatic radicals are exemplified by benzylpropyl, phenylethyl, phenoxyethyl and vinylbenzyl.

The G group may be hydrogen or an attached mono-, di-, oligo- or polysaccharide. Examples of suitable saccharides that can be oxidized to sugar acids $[GOCH_2(CHOG)_nCOOH]$ include but are not limited to, erythrose, threose, ribose, arabinose, xylose, lyxose, allose, altrose, idose, talose, glucose, galactose, mannose, gulose, fructose, sorbose, sucrose, isomaltose, isomalt, isomaltulose (palatinose), trehalulose, 3-ketosucrose, leucrose, lactulose, gentiobiose, maltose, lactose, melibose, cellobiose, triglucose (maltotriose), tetraglucose, starch and cellulose.

When an amino group is present it may be converted to the corresponding salt by reaction with, for example an organic or inorganic acid such as hydrochloric acid, sulfuric acid, phosphoric acid, boric acid, oxalic acid, malonic acid, glutaric acid, adipic acid, sebacic acid, tricarballylic acid, butanetetracarboxylic acid, itaconic acid, maleic acid, malic acid, fumaric acid, citraconic acid, glutaconic acid, bis(hydroxymethyl)propionic acid, tartaric acid, citric acid, formic acid, lactic acid, acetic acid, benzoic acid, methanesulfonic acid, ethanesulfonic acid, toluenesulfonic acid and mixtures thereof or by reaction with, for example an alkylating agent such as chloromethane, dimethyl sulfate, diethyl sulfate and benzyl chloride.

The amino group may also be amidated with an alkyl anhydride, mixed alkyl anhydride or other activated fatty acids to form a heteroatom containing alkyl aldonamide compound that is structurally different from prior art alkyl aldonamides.

The heteroatom containing alkyl aldonamide compounds of the present invention can also be ethoxylated, propoxylated or butoxylated with ethylene oxide, propylene oxide, butylene oxide or mixtures thereof to give a series of polyoxyalkylene ether sugar surfactants.

While not wishing to be bound by theory, it is believed that the amphiphilic nature of alkyl aldonamides and aldobionamides cause them to concentrate at the surface interface thereby reducing the free energy of the system. However, when all available interfaces are saturated, the overall energy reduction may be through precipitation into insoluble solids or through soluble micelle formation. In general, the preferred interfacial phenomena is micellization since certain surfactant benefits such as solubilization of soils (detergency), foam production, surfactant solubility in composition matrixes, surface tension reduction etc., strongly depend on the existence of these aggregates in solution. Compounds that precipitate out of solution do not form micelles and therefore can not provide favorable surfactant benefits. Instead, such compounds are useful as pearlescent agents, opacifiers and suspending agents. In addition, it is also favorable for micellization to occur at low temperature (low Krafft temperatures), since prior art aldonamides which lack a heteroatom in the alkyl chain as seen in Examples 1 through 22, have an unfavorable heat of hydration or high Krafft point and precipitate out of aqueous solution rendering them ineffective and useless as surfactants but instead useful as pearlescent agents, opacifiers and suspending agents.

Pearlescent agents and opacifiers function to provide detergent, personal product and oral hygiene compositions with a soft, silvery and pearly luster which often has very favorable consumer appeal.

Suspending agents function to provide detergent, personal product and oral hygiene compositions with a uniform suspension of certain performance ingredients (e.g. zinc pyridinethione, silicone fluid etc.), thereby assisting in the delivery of desirable performance attributes associated with these ingredients.

It has now been found that the addition of heteroatoms such as an amine (NH), amine salt (NHA+), oxygen (O), ester (COO or OOC), substituted amide (NACO, CONA or NCOA), wherein A is hydrogen (H) or a $C_1$–$C_{18}$ alkyl group that may optionally contain a hydroxyl group, in the alkyl chain of an aldonamide or aldobionamide compound unexpectedly reduces the packing constraints of these materials in the solid state. The net result is a more favorable heat of hydration, lower Krafft point, enhanced water solubility, increased rate of micellization, low surface tension, measurable critical micelle concentration and superior foaming performance.

Also, closer observation will reveal that compounds of the invention allow the introduction of the same or greater alkyl chain length (differing only by the presence of the heteroatom) without simultaneously sacrificing the foaming and solubility characteristics of such compounds.

These findings are quite unexpected and have not been recognized or appreciated in the art.

General Method of Manufacture

Aldonic acids, aldobionic acids and their lactones are prepared by microbial fermentation, chemical oxidation or enzymatic oxidation of sugars. [See for example, EP 142, 725 (1985) to Saito. et al.; EP 232,202 (1986) and EP 233,816 (1987) to Fuertes et al.; JP 62/269728 (1987) to Kimura, et al.; Biotechnology Letters 6:487 (1984) to Chang, et al.: Biotechnology Letters 9:252 (1987) to Burdick, et al.: German Pat. No. 2,911,192 (1980) and U.S. Pat. No. 4,460,686 (1984) to Hartmeier and Appl. Microbiol. Biotechnol. 21:356 (1985) to Seiskari. et al. all of which are incorporated herein by reference]. Examples of aldonic acids, aldobionic acids and their lactones suitable for the preparation of heteroatom containing alkyl aldonamide compounds include but are not limited to threonic acid, arabinonic acid, lyxonic acid, allonic acid, altronic acid, idonic acid, talonic acid, gluconic acid, galactonic acid, mannonic acid, lactobionic acid, maltobionic acid, cellobionic acid, gentiobionic acid, melibionic acid, glucopyranosyl-(1–5)-arabinonic acid, erythronolactone, ribonolactone, xylonolactone, gluconolactone, galactonolactone, mannonolactone, gulonolactone, glucoheptonolactone, lactobionolactone maltobionolactone, maltotrionolactone, maltopentonolactone and the like.

Heteroatom containing alkyl aldonamide compounds of the invention are prepared by reaction of the appropriate heteroatom containing amine with an aldonic acid or aldobionic acid (preferably with the corresponding aldonolactone or aldobionolactone) in an organic solvent (such as methanol) with or without an acid catalyst (such as methanesulfonic acid) at about 0° C. to about 90° C., preferably at about 20° C. to about 70° C., even more preferably at about 30° C. to about 60° C.

Heteroatom containing alkyl aldonamide salt compounds of the invention are prepared by reaction of an alkylaminoalkyl aldonamide or aldobionamide compound with an organic or inorganic acid in water or organic solvent at about 0° C. to about 100° C. preferably at about 20° C. to about 70° C. even more preferably at about 25° C. to about 55° C.

Additional general methods of manufacture are described in EP Application Nos. 0,550,106, 0,550,278, 0,550,281 and 0,551,675 to Au et al.: 0,569,869 to Gerling et al.: U.S. Pat. Nos. 5,310,542, 5,296,588 and 5,336,765 to Au et al. all of which are incorporated herein by reference.

All raw materials such as D-gluconolactone. D-glucoheptonolactone, D-lactobionolactone, D-maltobionolactone, alkyloxypropylamine, alkylaminopropylamine and alkyloxypropylaminopropylamine are available in bulk and the end products are easily prepared by the commercially feasible process described above.

Processing may be continuous or batch wise, however cost savings may be further increased through continuous processing by virtue of economy of scale.

Method of Manufacture of Alkylamidoalkyl Aldonamides

In the third embodiment of the invention, a new and improved process for the manufacture of alkylamidoalkyl aldonamides and the like is described.

It has been found, in accordance with the present invention, that novel alkylamidoalkyl aldonamides may be readily prepared by reacting amino heteroatom containing alkyl aldonamides such as alkylaminoalkyl aldonamides, alkyloxyalkylaminoalkyl aldonamides, alkyloxyalkyloxyalkylaminoalkyl aldonamides, alkyl(polyoxyalkyl)aminoalkyl aldonamides, [also known as alkyl(polyoxyalkylene)aminoalkyl aldonamides], alkylamidoalkylaminoalkyl aldonamides and the like with alkyl anhydrides at elevated temperature in the presence of water or an organic solvent in the absence or presence of base followed by the addition of a bleaching or reducing agent. The invention can be more readily understood when reference is made to the general equation:

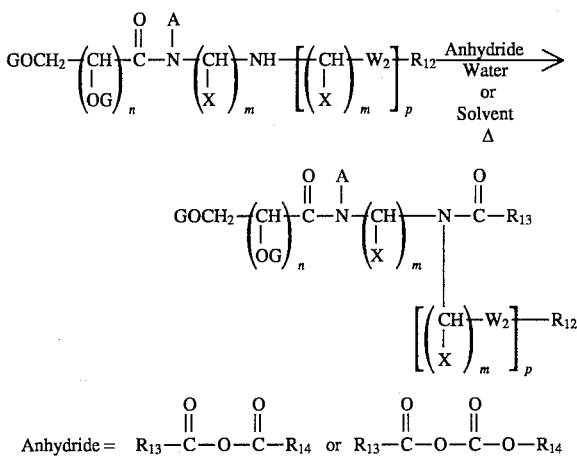

The method is especially suitable for the manufacture of alkylamidoalkyl aldonamides wherein:

n=1–6;
m=1–6;
X=H, a $C_1$–$C_4$ alkyl group or mixtures thereof;
$W_2$=amine (NH), amine salt (NHA+), ether 10), sulfur (S), sulfur monoxide (SO), sulfur dioxide ($SO_2$), amide (NACO, CONA or NCOA) group or mixtures thereof;
p=0–25;
G=H, a mono-, di-, oligo-, polysaccharide group, a $(CH_2CH_2O)_q$—H, $(CH_2CHCH_3O)_r$—H group or mixtures thereof;
q=1–50;
r=1–50;
A=H, a hydroxy $C_1$–$C_{18}$ alkyl group, a $C_1$–$C_{18}$ straight or branched chain, saturated or unsaturated hydrocarbon which may be unsubstituted or substituted with an aromatic, cycloaliphatic, mixed aromatic aliphatic radical or mixtures thereof;

$R_{12}$ is a straight or branched chain, saturated or unsaturated hydrocarbon which may be unsubstituted or substituted with an aromatic, cycloaliphatic, or mixed aromatic aliphatic radical comprising from about 1 to about 30 carbon atoms;

$R_{13}$, and $R_{14}$ is a straight or branched chain, saturated or unsaturated hydrocarbon or fluorocarbon which may be unsubstituted or substituted with an aromatic, cycloaliphatic, or mixed aromatic aliphatic radical comprising from about 2 to about 18 carbon atoms. $R_{13}$, and $R_{14}$ may be the same or different, or they may be combined to form a cyclic anhydride.

Preferably:
n=1–5;
m=1–5;
X=H, a $C_1$–$C_2$ alkyl group or mixtures thereof;
$W_2$=amine (NH), amine salt (NHA+), ether (O), amide (NACO, CONA or NCOA) group or mixtures thereof;
p'=0–5;
G=H, a monosaccharide or mixtures thereof;
A=H, a hydroxy $C_1$–$C_{10}$ alkyl group, a $C_1$–$C_{10}$ straight or branched chain, saturated or unsaturated hydrocarbon group or mixtures thereof;
$R_{12}$ is a straight or branched chain, saturated or unsaturated hydrocarbon which may be unsubstituted or substituted with an aromatic, cycloaliphatic, or mixed aromatic aliphatic radical comprising from about 4 to about 28 carbon atoms;
$R_{13}$ and $R_{14}$ is a straight or branched chain, saturated or unsaturated hydrocarbon or fluorocarbon which may be unsubstituted or substituted with an aromatic, cycloaliphatic, or mixed aromatic aliphatic radical comprising from about 2 to about 10 carbon atoms. $R_{13}$ and $R_{14}$ may be the same or different, or they may be combined to form a cyclic anhydride.

More preferably:
n=2–5;
m=1–4;
X=H, a $C_1$ alkyl group or mixtures thereof;
$W_2$=amine (NH), amine salt (NHA,), ether (O), amide (NACO, CONA or NCOA) group or mixtures thereof;
p'=0–4;
G=H, a monosaccharide or mixtures thereof;
A=hydrogen (H) or a $C_1$–$C_8$ alkyl group that optionally may contain a hydroxyl group;
$R_{12}$ is a straight or branched chain, saturated or unsaturated hydrocarbon comprising from about 6 to about 24 carbon atoms;
$R_{13}$ and $R_{14}$ is a straight or branched chain, saturated or unsaturated hydrocarbon or fluorocarbon radical comprising from about 2 to about 8 carbon atoms. $R_{13}$ and $R_{14}$ may be the same or different, or they may be combined to form a cyclic anhydride.

Most preferably:
n=3–5;
m=1–3;
X=H, a $C_1$ alkyl group or mixtures thereof;
$W_2$=amine (NH), amine salt (NHA+), ether (O) group or mixtures thereof;
p'=1–3;
G=H, a monosaccharide or mixtures thereof;
A=hydrogen (H) or a $C_1$–$C_6$ alkyl group that optionally may contain a hydroxyl group;
$R_{12}$ is a straight or branched chain, saturated or unsaturated hydrocarbon comprising from about 8 to about 22 carbon atoms;
$R_{13}$ and $R_{14}$ is a straight or branched chain, saturated or unsaturated hydrocarbon or fluorocarbon radical comprising from about 2 to about 6 carbon atoms. $R_{13}$ and $R_{14}$ may be the same or different, or they may be combined to form a cyclic anhydride.

Examples of alkylaminoalkyl aldonamides suitable for this method include but are not limited to octylaminopropyl gluconamide, nonylaminopropyl gluconamide, decylaminopropyl gluconamide, undecylaminopropyl gluconamide, dodecylaminopropyl gluconamide, tridecylaminopropyl gluconamide, tetradecylaminopropyl gluconamide, pentadecylaminopropyl gluconamide, hexadecylaminopropyl gluconamide, octyldecylaminopropyl gluconamide, oleylaminopropyl gluconamide, linoleyl aminopropyl gluconamide, cocoaminopropyl gluconamide, soyaaminopropyl gluconamide, tallowaminopropyl gluconamide, castoraminopropyl gluconamide, decyloxypropylaminopropyl gluconamide, dodecyloxypropylaminopropyl gluconamide, tridecyloxypropylaminopropyl gluconamide, tetradecyloxypropylaminopropyl gluconamide, pentadecyloxypropylaminopropyl gluconamide, $C_8$–$C_{18}$ di(oxyethyl)aminopropyl gluconamide, $C_8$–$C_{18}$ penta(oxyethyl)aminopropyl gluconamide, $C_8$–$C_{18}$ deca(oxyethyl)aminopropyl gluconamide, $C_8$–$C_{18}$ poly(oxyethylene)aminopropyl gluconamide, $C_8$–$C_{18}$ amidoethylaminoethyl gluconamide, $C_8$–$C_{18}$ amidoethyldi(aminoethyl) gluconamide, octylaminopropyl laetobionamide, decylaminopropyl lactobionamide, dodecylaminopropyl gluconamide, tetradecylaminopropyl lactobionamide, hexadecylaminopropyl lactobionamide, octyldecylaminopropyl lactobionamide, oleylaminopropyl lactobionamide, linoleylaminopropyl lactobionamide, cocoaminopropyl lactobionamide, soyaaminopropyl lactobionamide, tallowaminopropyl lactobionamide, castoraminopropyl lactobionamide, decyloxypropylaminopropyl laetobionamide, dodecyloxypropylaminopropyl lactobionamide, tridecyloxypropylaminopropyl lactobionamide, tetradecyloxypropylaminopropyl lactobionamide, pentadecyloxypropylaminopropyl lactobionamide, $C_8$–$C_{18}$ tri(oxyethyl)aminopropyl lactobionamide, $C_8$–$C_{18}$ tetra(oxyethyl)aminopropyl lactobionamide, $C_8$–$C_{18}$ hexadeca(oxyethyl)aminopropyl lactobionamide, $C_8$–$C_{18}$ oxyethylenedi(oxypropylene)oxypropyl lactobionamide, $C_8$–$C_{18}$ tri(oxypropylene)oxypropyl lactobionamide, $C_8$–$C_{18}$ tetra(oxypropylene)di(oxyethylene)tri(oxypropylene)oxypropy lactobionamide, $C_8$–$C_{18}$ amidoethylaminoethyl lactobionamide, $C_8$–$C_{18}$ aminopropyl maltobionamide, $C_8$–$C_{18}$ oxypropylaminopropyl maltobionamide, $C_8$–$C_{18}$ amidoethylaminoethyl maltobionamide, $C_8$–$C_{18}$ aminopropyl glyceramide, $C_8$–$C_{18}$ aminopropyl glucoheptonamide, $C_8$–$C_{18}$ oxypropylaminopropyl glucoheptonamide, $C_8$–$C_{18}$ poly(oxyethylene)poly(oxypropylene)oxypropyl lactobionamide and mixtures thereof. Any alkyl aldonamide compound can be used, as long as the aldonamide compound has at least one amino group in or on the alkyl chain (or near or on the sugar head group) available for amidation.

Examples of linear alkyl anhydrides (linear acid anhydrides) suitable for this method include, but are not limited to acetic anhydride, propionic anhydride, butyric anhydride, valeric anhydride, caproic anhydride, enanthic anhydride, caprylic anhydride, pelargonic anhydride, capric anhydride, lauric anhydride, myristic anhydride, palmitic anhydride, stearic anhydride, oleic anhydride, linoleic anhydride, docosanoic anhydride, isobutyric anhydride, 2-methylbutyric anhydride, isobutenyl anhydride, trimethylacetic anhydride, crotonic anhydride, methacrylic anhydride, chloroacetic anhydride, trichloroacetic anhydride, trifluroacetic anhydride, pentafluoropropionic anhydride, heptafluorobutyric anhydride; cyclic anhydrides (cyclic acid anhydrides) such as glutaric anhydride, 3-methylglutaric anhydride, 2,2-dimethylglutaric anhydride, 3,3-dimethylglutaric anhydride, 3-ethyl-3-methylglutaric anhydride, hexafluoroglutaric anhydride, succinic anhydride, methylsuccinic anhydride, 2,2-dimethylsuccinic anhydride, isobutenylsuccinic anhydride, S-acetylmercaptosuccinic anhydride, $C_2$–$C_{18}$ alkylsuccinic anhydride, $C_2$–$C_{18}$ alkylenesuccinic anhydride, $C_1$–$C_{18}$ alkyloxypolyoxyethylenesuccinic anhydride, 3,5-diacetyltetrahyropyran- 2,4,6-anhydride, phthalic anhydride, hexahydro-4-methylphthalic anhydride, cis-1,2,3,6tetrahydrophthalic anhydride, 3,4,5,6-tetrahydrophthalic anhydride, 4-methylphthalic anhydride, 3,6-difluorophthalic anhydride, 3,6-dichlorophthalic anhydride, 4,5-dichlorophthalic anhydride, 3-hydroxyphthalic anhydride, 4-nitrophthalic anhydride, maleic anhydride, 2,3-dimethylmaleic S-acetylmercaptosuccinic anhydride, citraconic anhydride, itaconic anhdyride, cis 1,2-cyclohexane dicarboxylic acid anhydride, trans 1,2-cyclohexane dicarboxylic anhydride, 1-cycopentene-1,2-dicarboxylic anhydride, 5-nor-bornene-2,3-dicarboxylic anhydride; and mixed alkyl anhydrides (carbonate carboxylic acid anhydrides or formate carboxylic acid anhydrides) such as ethyl hydrogen carbonate acetic anhydride, propyl hydrogen carbonate acetic anhydride, butyl hydrogen carbonate propionic anhydride, isobutyl hydrogen carbonate butyric anhydride, ethyl hydrogen carbonate valeric anhydride, methyl hydrogen carbonate caproic anhydride, ethyl hydrogen carbonate enanthic anhydride, heptyl hydrogen carbonate caprylic anhydride, ethyl hydrogen carbonate pelargonic anhydride, ethyl hydrogen carbonate capric anhydride, propyl hydrogen carbonate lauric anhydride, ethyl hydrogen carbonate myristic anhydride, ethyl hydrogen carbonate palmitic anhydride, ethyl hydrogen carbonate stearic anhydride, ethyl hydrogen carbonate oleic anhydride, ethyl hydrogen carbonate linoleic anhydride, ethyl hydrogen carbonate docosanoic anhydride, isopropyl hydrogen carbonate isobutyric anhydride, ethyl hydrogen carbonate 2-methylbutyric anhydride, ethyl hydrogen carbonate isobutenyl anhydride, ethyl hydrogen carbonate isotridecyl anhydride, hexyl hydrogen carbonate trifluroacetic anhydride, ethyl hydrogen carbonate pentafluoropropionic anhydride, ethyl hydrogen carbonate heptafluorobutyric anhydride, ethyl hydrogen carbonate $C_1$–$C_{18}$ alkylpolyoxyethylene anhydride, ethyl hydrogen carbonate $C_1$–$C_{18}$ alkylpolyoxypropylene anhydride, ethyl hydrogen carbonate $C_1$–$C_{18}$ alkylpolyoxyethylenepolyoxypropylene anhydride, butyl hydrogen carbonate acetic anhydride, isobutyl hydrogen carbonate acetic anhydride and the like or mixtures thereof.

When acetic anhydride, trifluroacetic anhydride, ethyl hydrogen carbonate acetic anhydride and the like are used, they may leave in some instances, a residual odor of acetic acid. Often this can be covered up with perfume or prevented by neutralization with base. However, in some applications the presence of residual acetic acid odor is most undesirable. This can be further avoided by using an anhydride having a lower vapor pressure such as propionic anhydride, valeric anhydride, succinic anhydride, maleic anhydride and the like.

The alkyl anhydrides represent a preferred amidating reagent of the invention, however other "activated" fatty acids can be used as well and may be suitable in certain cases. Examples of other activated fatty acids that are known or become known, include but are not limited to, fatty acid halides, 2-acylthio-5-methyl-1,3,4-thiadiazoles, 3-acyl-5-methyl- 1,3,4-thiadiazole-2-(3-H)-thiones, N-hydroxysuccinimide activated carboxylic acids and the like.

Examples of fatty acid halides, include but are not limited to $C_2$–$C_{18}$ alkyl acid chloride, $C_2$–$C_{18}$ alkyl acid bromide, oleic acid chloride, linoleic acid chloride, coconut acid chloride, soya acid chloride, tallow acid chloride, castor acid chloride, cottonseed acid chloride, palm acid chloride, rapeseed acid chloride, $C_1$–$C_{18}$ alkyl polyoxyethylene acid chloride, $C_1$–$C_{18}$ alkyl polyoxypropylene acid chloride, $C_1$–$C_{18}$ alkyl polyoxypropylenepolyoxyethylene acid chloride and the like.

Examples of 2-acylthio-5-methyl-1,3,4-thiadiazoles, include but are not limited to those of the general formula:

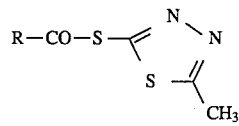

wherein R is a $C_1$–$C_{18}$ straight or branched chain, saturated or unsaturated hydrocarbon which may be unsubstituted or substituted with an aromatic, cycloaliphatic, mixed aromatic aliphatic radical, or polyoxyalkylene radical or mixtures thereof.

Examples of 3-acyl-5-methyl-1,3,4-thiadiazole-2-(3H)-thiones, include but are not limited to those of the general formula:

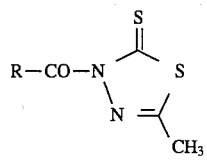

wherein R is a $C_1$–$C_{18}$ straight or branched chain, saturated or unsaturated hydrocarbon which may be unsubstituted or substituted with an aromatic, cycloaliphatic, mixed aromatic aliphatic radical, or polyoxyalkylene radical or mixtures thereof.

Examples of N-hydroxysuccinimide activated carboxylic acids, include but are not limited to those of the general formula:

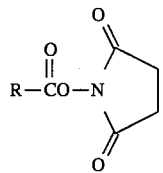

wherein R is a $C_1$–$C_{18}$ straight or branched chain, saturated or unsaturated hydrocarbon which may be unsubstituted or substituted with an aromatic, cycloaliphatic, mixed aromatic aliphatic radical, or polyoxyalkylene radical or mixtures thereof. Methods of using such activated carboxylic acids as amidating agents are described in French Patent No. 2,657, 611 to Plusquellec et al., Tetrahedron Letters 32 (12), 1557 (1991) to Leon-Ruaud et al. and Analytical. Biochemistry 212, 117 (1993) to Brenner-Hénaff et al. which are all incorporated herein by reference.

Within the process of the invention, it is desirable to use water-free reaction components, but this is not a necessary condition. Also, within the process of the invention, the alkylaminoalkyl aldonamide can be added progressively to the anhydride, or the anhydride can be added progressively to the alkylaminoalkyl aldonamide, preferably however, both reagents are added in full amount at the beginning of the reaction. The alkylaminoalkyl aldonamide can be used in stoichiometric (equal) molar amounts relative to the anhydride, or the anhydride can be used in molar excess relative to the alkylaminoalkyl aldonamide, preferably however, as seen in Examples 46 through 51, the anhydride is used in molar excess relative to the alkylaminoalkyl aldonamide. The molar excess of anhydride to alkylaminoalkyl aldonamide is from about 7:1 to about 1:1, preferably from about 5:1 to about 1.1:1, more preferably from about 3:1 to about 1.2:1. The use of excess alkyl anhydride is satisfactory and can drive the reaction to completion.

The alkylaminoalkyl aldonamide or anhydride is preferably in crystalline to liquid form respectively, however solid, flake, paste, gel or granular form can be used as well.

The reaction can be performed at or below room temperature, however shorter reaction times can be achieved at elevated temperature and is usually preferred. Favorable reaction temperatures are from about 0° C. to about 100° C., preferably from about 10° C. to about 90° C., most preferably from about 20° C. to about 80° C.

The reaction can be carried out under pressure to assist in the overall reaction rate, however, it is preferably carried out at atmospheric pressure and under an inert gas blanket such as nitrogen, argon or helium, most preferably it is carried out at atmospheric pressure.

The substrates are reacted with intensive stirring for several hours, preferably from about 96 hours to about 0.5 hour, more preferably from about 48 hours to about 1 hour, most preferably when the reaction is complete and is verified by an analytical technique such as thin layer chromatography (TLC), infrared spectroscopy (IR), proton nuclear magnet resonance ($H^1$ NMR), carbon 13 nuclear magnet resonance (Cla NMR), direct chemical ionization mass spectrometry (DCI MS), fast atom bombardment mass spectrometry (FAB MS), high pressure liquid chromatography (HPLC) and the like.

An alkaline neutralizing agent or alkaline catalyst can be optionally used to maintain a neutral pH or to accelerate the rate of the reaction. These materials are generally classified as an organic or inorganic bases. Examples of suitable alkaline neutralizing agents/catalysts useful in the present method include, but are not limited to sodium hydroxide, potassium hydroxide, ammonium hydroxide, calcium hydroxide, magnesium hydroxide, sodium metal, potassium metal, sodium methoxide, potassium methoxide, sodium ethoxide, potassium ethoxide, sodium carbonate, potassium carbonate, ammonium carbonate, magnesium carbonate, calcium carbonate, lithium carbonate, sodium bicarbonate, potassium bicarbonate, ammonium bicarbonate, magnesium bicarbonate, calcium bicarbonate, trisodium phosphate, tripotassium phosphate, tetrasodium pyrophosphate, tetrapotassium pyrophosphate, pentasodium tripolyphosphate, pentapotassium tripolyphosphate, disodium tartrate, dipotassium tartrate, sodium potassium tartrate, trisodium citrate, tripotassium citrate, sodium acetate, potassium acetate, sodium valerate, sodium laurate, potassium laurate, sodium myristate, potassium myristate, sodium stearate, sodium oleate, sodium 12-hydroxydodeconate, sodium 2,2-dimethylbutyrate, disodium oxalate, dipotassium oxalate, disodium malonate, dipotassium malonate, disodium succinate, dipotassium succinate, disodium dodecyl succinate, disodium glutarate, dipotassium glutarate, disodium 1,12-dodecanedicarboxylate, trisodium tricarballylate, tripotassium tricarballylate, tetrasodium 1,2,3,4-butanetetracarboxylate, tetrapotassium 1,2,3,4-butanetetracarboxylate, disodium itaconate, dipotassium itaconate, disodium maleate, dipotassium maleate, disodium fumarate, dipotassium fumarate, disodium malate, disodium agaricate, dipotassium agaricate, sodium ethoxyacetate, sodium glyoxylate, sodium 4-acetylbutyrate, sodium cyclohexylacetate, trisodium 1,3, 5-cyclohexanetricarboxylate, sodium basic silicates, potassium basic silicates, sodium basic aluminosilicates, potassium basic aluminosilicates, sodium lactate, potassium lactate, ammonium lactate, sodium glycinate, sodium dimethylglycinate, pentasodium diethylenetriaminepentaacetate (DTPA), tetrasodium ethylenediaminetetraacetate (EDTA), tetrapotassium ethylenediaminetetraacetate, calcium disodium ethylenediaminetetraacetate, triethylamine, tripropylamine, tributylamine, trioctylamine, N,N-dimethyldodecylamine, N,N'-diethylethylenediamine, N,N-diethyl-N'-methylethylenediamine, N,N,N',N'-tetramethylethylenediamine, N,N,N',N'-tetraethylethylenediamine, N,N,N',N'-tetramethylethylenediamine, N,N,N',N'-tetraethyl-1,3-propanediamine, triethanolamine, diethanolamine, pyridine, morpholine, picoline, collidine, ethylpiperidine diethylcyclohexylamine and the like. Mixtures of base catalysts can be also used as well and may be preferred in certain cases. Preferred base neutralizing agents/catalysts include sodium hydroxide, potassium hydroxide, sodium methoxide, sodium ethoxide, sodium carbonate, sodium bicarbonate, disodium oxalate, sodium acetate, triethanolamine, triethylamine, tripropylamine and mixtures thereof.

When the base is used a neutralizing agent, it can be added at any time during the reaction, however it is preferably added during the reaction portionwise (to maintain a neutral pH) or at the end of the reaction in full amount. The molar ratio of alkyl anhydride (or alkyl acid) to alkaline neutralizing agent is from about 2:1 to about 0.7:1, preferably from about 1.6:1 to about 0.8: 1, most preferably from about 1.3:1 to about 0.9:1.

When the base is used as a catalyst, it can be added at any time during the reaction, however it is preferably added at the beginning of the reaction and in full amount. The use of an alkaline catalyst can also enhance the rate of esterification of hydroxyl groups on the sugar head group, which are themselves, innocuous and colorless, and so they can remain in the finished product (in low amounts) without need for further purification or in certain cases they may be removed by hydrolysis. The molar ratio of alkyl anhydride to base catalyst is from about 500:1 to about 20:1, preferably from about 300:1 to about 100:1, most preferably from about 250:1 to about 150:1.

In general, water or an organic solvent can be used to perform the reaction of the present invention.

When water is used, the quantity of water should be sufficient to dissolve the carbohydrate and anhydride, but otherwise this is not an essential condition. After the reaction is deemed complete, water may be removed by freeze drying, spray drying, or vacuum distillation, however it may be more economical to leave the water in and use it as a diluent making the product a pureable liquid. Typical levels of water used as a reaction solvent or diluent are from about 5% to about 95%, preferably from about 15% to about 70%, most preferably from about 20% to about 60% by weight of the total reaction mixture.

When an organic solvent is used, the quantity of solvent should be sufficient to dissolve the carbohydrate and anhydride, but otherwise this is not an essential condition. Typical levels of solvent used are from about 5% to about 98%, preferably from about 15% to about 75%, most preferably from about 20% to about 65% by weight of the total reaction mixture. Preferably the solvent is removed (after the reaction is complete) by known procedures such as simple distillation, vacuum distillation or rota-evaporation.

However, this may not be feasible when high boiling materials, such as propylene glycol, ethylene glycol, diethylene glycol, polyethylene glycol and the like are used as solvents, or when other useful composition ingredients such nonionic surfactants, sorbitol and the like, are used as pseudo-solvents or phase transfer agents. These materials are preferably left in the finished product and generally do not present a problem. In fact, in some cases, it may be more beneficial.

In general, certain nonionic alkylamidoalkyl aldonamide surfactants of the present invention are isolated as solids (by gravity filtration, vacuum filtration, centrifugation or other separation techniques), however when syrups are obtained, crystallization may be enhanced by the addition of an organic solvent. The resulting product is subsequently filtered, washed with an organic solvent and air or vacuum dried.

Optionally, further purification of (solid) alkylamidoalkyl aldonamide surfactants can be performed by recrystallization in an organic solvent. The amount of solvent used is sufficient to dissolve the product, preferably with heating. The solution is then slowly cooled until recrystallization is complete, subsequently filtered, washed with an organic solvent and air or vacuum dried.

Still optionally, further purification of alkylamidoalkyl aldonamide surfactants can be performed by column chromatography. A preferred version of this method involves passing a solution of alkylamidoalkyl aldonamide through a column containing an acidic ionic exchange resin which can capture the unreacted alkylaminoalkyl aldonamide, followed by passing through a column containing a basic ionic exchange resin which can capture the (fatty)alkyl add byproduct obtained form the alkyl anhydride. Water or solvent is used to assist in the removal of the alkylamidoalkyl aldonamide from the column to provide an eluate. If water is used, it may be left in, or partially removed from the eluate. If a solvent is used, it may be partially or completely removed from the eluate by simple distillation, vacuum distillation or rotaevaporation. If the product precipitates out of solution during solvent removal, it is preferably filtered, washed with an organic solvent and air or vacuum dried. The substrates left on the ionic exchange resin can be recovered by washing the resin with an appropriate solution of base or acid, which are then separated, optionally purified and recycled. Similar methods of purification are described in U.S. Pat. Nos. 5,296,588 and 5,336,765 to Au et al. which are both incorporated herein by reference.

Typical examples of ionic exchange resin useful for ionic exchange chromatography include, but are not limited to Amberlite CG-50, Amberlite CG-420, Amberlite IR- 118, Amberlite IR- 120, Amberlite IR- 120 (Plus), Amberlite IRA-68, Amberlite IRA-400, Amberlite IRA-410, Amberlite IRA-743, Amberlite IRA-900, Amberlite IRA-904, Amberlite IRC-50S, Amberlite IRC-718, Amberlite IRP-64, Amberlite IRP-69, Amberlite MB-3A, Amberlyst 15, Amberlyst A-21, Amberlyst A-26, Amberlyst A-27, Amberlyst XN- 1010, Dowex 1×2-100, Dowex 1×2-200, Dowex 1×2-400, Dowex 1×8-50, Dowex 1×8-100, Dowex 1×8-200, Dowex 1×8-400, Dowex 50WX2-100, Dowex 50WX2-200, Dowex 50WX2-400, Dowex 50WX4-200 Dowex 50WX4-400, Dowex 50WX8-100, Dowex 50WX8-200, Dowex 50WX8-400 and the like.

Still optionally, further purification of alkylamidoalkyl aldonamide surfactants can also be performed by extraction from a mixture of water and organic solvent. A necessary criteria for extraction is that the organic solvent be immiscible with water. Preferably the alkylamidoalkyl aldonamide surfactant should be soluble in water and the alkyl anhydride and (fatty) alkyl acid should be soluble in the solvent, however this is not a necessary condition. The alkyl anhydride and (fatty) alkyl acid are then extracted into the solvent layer and removed from the aqueous layer containing the alkylamidoalkyl aldonamide surfactant. The water and organic layers are separated from each other, the solvent is removed, and the components in that solvent layer can be purified or recyclized. A mild vacuum is applied to the aqueous layer, removing any trace solvents, and the water is left with the final product free of alkyl acid and alkyl anhydride.

Typical reaction solvents, crystallization solvents, recrystallization solvents, washing solvents and eluting solvents that may be used include, but are not limited to acetic acid, acetone, acetonitrile, butanol, sec-butanol, tert-butanol, butyl acetate, butyl chloride, chloroform, cyclohexane, cyclopentane, dimethylformamide (DMF), dimethylacetamide, dimethylsulfoxide (DMSO), 2-ethoxy, ethanol, ethyl acetate, ethyl ether, ethylene glycol dimethyl ether (glyme), pentane, hexane, heptane, hexadecane, methanol, 2-methoxyethanol, 2-methoxyethyl acetate, methylethylketone (MEK), methylisoamylketone, methylisobutylketone, butylmethylketone, diisobutylketone, N-methyl-2-pyrrolidone, petroleum ether, propanol, isopropanol, propylene carbonate, pyridine, tetrachloroethylene, tetrahydrofuran (THF), tetramethylurea, toluene, trichloroethylene, 1,2,2-trichloro-1,2,2-trifluoroethane, 2,2,4-trimethylpentane, xylene, ethanol, pentyl acetate, carbon disulfide, 1-chlorobutane, 1,2-dichloroethane, 1,2-dimethoxyethane, glycerol, methylcyclohexane, ethylene glycol, furan, 1,2-dimethoxyethane, propylene glycol (1,2-propanediol), 1-chloro-1,1-difluoroethane, isopropylbenzene (cumene), cyclohexanol, cyclohexanone, 4-hydroxy-4-methyl-2-pentanone (diacetone alcohol), diethylene glycol, diisopropyl ether, ethylene glycol monobutyl ether (2-butoxyethanol), ethylene glycol monomethyl ether (2-methoxyethanol), hexylene glycol, isopentyl acetate, isobutyl acetate, isopropyl acetate, methyl acetate, methylpentylketone and the like, however, alcohols are the preferred reaction solvents and acetone, acetates or alcohols are the preferred recrystallization/washing solvents. Mixtures of solvents can be used as well and may be preferred in certain cases. Mixtures of solvents are useful in obtaining a desired polarity which may not be easily achieved through use of individual solvents. Optimum polarity is most useful during crystallization and recrystallization.

Optionally, the reaction may also be carried out in the presence of phase transfer agent, such as a typical ethoxylated/propoxylated surfactant (e.g. ethoxylated alcohol, ethoxylated/propoxylated alcohol, propoxylated alcohol, sorbitan ester etc.) which provides a homogeneous reaction phase. A comprehensive list of surfactants that are useful as phase transfer agents are described in McCutcheon's, Detergents and Emulsifiers (Vol 1), 1993 North American Edition and McCutcheon's, Detergents and Emulsifiers (Vol 1), 1993 International Edition, published by McCutcheon's MC Publishing Co. which are both incorporated herein by reference.

When water is used, the reaction is preferably done in the presence of alkaline neutralizing agent which is used to maintain a pH of about 7. When the reaction is complete, a mild vacuum may be applied to remove excess unreacted alkyl anhydride and any excess base may be optionally neutralized with an organic or inorganic: acid, however this may not be a necessary condition since the by-product from the anhydride is usually a (fatty) alkyl acid compound.

When an organic solvent is used, the reaction can be done in the absence or presence of alkaline catalyst which is used to accelerate the rate of the reaction. When the reaction is complete, the alkaline catalyst may be optionally neutralized with an organic or inorganic acid, however this may not be a necessary condition since the by-product from the anhydride is usually a (fatty) alkyl acid compound.

The neutralized (fatty) alkyl acid (usually a salt compound), is innocuous and can remain in the finished product. This mixture is suitable for formulation without further purification.

Examples of suitable neutralizing acids include, but are not limited to hydrochloric acid, sulfuric acid, phosphoric acid, boric acid, nitric acid, oxalic acid, malonic acid, glutaric acid, adipic acid, sebacic acid, tricarballylic acid, 1,2,3,4-butanetetracarboxylic acid, itaconic acid, maleic acid, malic acid, fumaric acid, citraconic acid, glutaconic acid, bis(hydroxymethyl)propionic acid, tartaric acid, citric acid, formic acid, lactic acid, acetic acid, benzoic acid, gluconic acid, glucoheptonic acid, lactobionic acid, maltobionic acid, coconut fatty acid, lauric acid, myristic acid, palmitic acid, valeric acid, 2-propylpentanoic acid, succinic acid, dodecenyl succinic acid, arotonic crotonic acid, tiglic acid, glycolic acid, ketomalonic acid, methoxyacetic acid, ethoxyacetic acid, 3-methoxypropionic acid, 6-nitrocaproic acid, levulinic acid, chelidonic acid, cyclobutanecarboxylic acid, 1,1-cyclohexanediacetic acid, glycine, phenylacetic acid, 3-benzoylpropionic acid, S-benzylthioglycolic acid, phenylmalonic acid, 2-hydroxyphenylacetic acid, toluenesulfonic acid, S-sulfobenzoic acid, 5-sulfoisophthalic acid, dodecylbenzenesulfonic acid, methanesulfonic acid, ethanesulfonic acid, propanesulfonic acid, dodecylsulfonic acid, 3-hydroxy-1-propanesulfonic acid, isethionic acid, ionic exchange resin and the like. Mixtures of acids can be used as well. Preferred neutralizing acids include hydrochloric acid, oxalic acid, tartaric acid, citric acid, formic acid, lactic acid, dodecylbenzenesulfonic acid and methanesulfonic acid. The amount of neutralizing acid used will be that which is sufficient to provide a pH in the range of about 4 to about 9, preferably from about 5 to about 8, most preferably about 7. Neutralization may be done in water or in an inert organic solvent or mixtures thereof at about 0° C. to about 35° C.

Bleaching is sometimes required but not always necessary, since compounds of the invention are generally of good color. Bleaching agents or peroxy compounds that may be used to further improve product color are hydrogen peroxide, sodium hypochlorite, potassium hypochlorite, calcium hypochlorite, lithium hypochlorite, dibasic magnesium hypochlorite, sodium hypobromite, chlorinated trisodium phosphate, hypochlorous acid, chlorine dioxide, sodium percarbonate, potassium percarbonate, sodium perborate monohydrate, sodium perborate tetrahydrate, oxone, t-butyl hydroperoxide, benzoyl peroxide, bis(trimethylsilyl)peroxide, peroxymonosulfate, peroxyformic add, peroxyacetic acid, peroxytrifluoroacetic acid, peroxybenzoic acid, m-chloroperoxybenzoic acid, peroxyphthalic acid, peroxymaleic acid, peroxypropionic acid, peroxylauric acid and the like. However, hydrogen peroxide and hydrogen peroxide liberating or generating compounds are preferred. Bleaching may be optionally done in water, in an inert organic solvent or mixtures thereof, before or during the reaction or after the reaction is complete, preferably however, bleaching is done after the reaction is complete at about 0° C. to about 75° C. in water or in an aqueous organic solvent system. Typical levels of beaching agent are from about 0.01% to about 7%, preferably from about 0.02% to about 5%, even more preferably from about 0.03% to about 3% by weight of the total reaction mixture.

Color improvement may also be carried out by using reducing agents belonging to two classes.

The first class of agents comprises compounds which include sulfur in the +4 oxidation state and show a negative oxidation relative to hydrogen. Illustrative of this class are salts of sulfite, bisulfite, hydrosulfite (dithionite), metabisulfate (pyrosulfite) and mixtures thereof. Suitable salt counter ions include alkali metal, alkaline earth metal, ammonium, alkyl- or hydroxyalkylammonium cations and mixtures thereof. Specific examples include, but are not limited to sodium sulfite, potassium sulfite, calcium sulfite, sodium bisulfite (sodium hydrogen sulfite), potassium bisulfite, sodium hydrosulfite, zinc hydrosulfite, sodium metabisulfite and potassium metabisulfite. Sulfur dioxide, sulfurous acid and sodium sulfoxylate formaldehyde are useful as well.

The second class of reducing agents includes those compounds having hydrogen in the −1 oxidation state and show a negative oxidation potential relative to hydrogen. Illustrative of this class are sodium hydride, potassium hydride, calcium hydride, lithium hydride, magnesium hydride, sodium borohydride, sodium cyano borohydride, potassium borohydride, lithium borohydride, magnesium borohydride, alkyl- and alkoxy borohydrides, aluminum hydride, sodium aluminum hydride, potassium aluminum hydride, calcium aluminum hydride, lithium aluminum hydride, alkyl- and alkoxy aluminum hydrides such as sodium dihydrobis(2-methoxyethoxy)aluminate, diboranes and mixtures thereof. Particularly preferred among the foregoing are the bisulfites and borohydrides, most especially preferred are sodium bisulfite and sodium borohydride and mixtures thereof. Reduction may be optionally done in water or in an inert organic solvent before or during the reaction or after the reaction is complete, preferably however, reduction is done without water or an organic solvent and after the reaction is complete at about 0° C. to about 100° C. Typical levels of reducing agent are from about 0.01% to about 7%, preferably from about 0.02% to about 5%, even more preferably from about 0.03% to about 3% by weight of the total reaction mixture.

The alkylamidoalkyl aldonamide compounds prepared by the method of the invention are generally isolated as crystalline solids in good yield, high purity and desirable color.

Home Application and Use

The heteroatom containing alkyl aldonamide compounds of the present invention are useful in detergent, personal product, oral hygiene, food and pharmacological compositions which are available in a variety of types and forms. Preferred applications are detergent, personal product and oral hygiene compositions.

A classification according to detergent type would consist of heavy-duty detergent powders, heavy-duty detergent liquids, light-duty liquids (dishwashing liquids), institutional detergents, specialty detergent powders, specialty detergent liquids, laundry aids, pretreatment aids, after treatment aids, presoaking products, hard surface cleaners, carpet cleansers, carwash products and the like.

A classification according to personal product type would consist of hair care products, bath products, cleansing products, skin care products, shaving products and deodorant/antiperspirant products.

Examples of hair care products include, but are not limited to rinses, conditioners shampoos, conditioning shampoos, antidandruff shampoos, antilice shampoos, coloring shampoos, curl maintenance shampoos, baby shampoos, herbal shampoos, hair loss prevention shampoos, hair growth/promoting/stimulating shampoos, hairwave neutralizing shampoos, hair setting products, hair sprays, hair styling products, permanent wave products, hair straightening/relaxing products, mousses, hair lotions, hair tonics, hair promade products, brilliantines and the like.

Examples bath products include, but are not limited to bath oils, foam or bubble bathes, therapeutic bathes, after bath products, after bath splash products and the like.

Examples cleansing products include, but are not limited to shower cleansers, shower gels, body shampoos, hand/body/facial cleansers, abrasive scrub cleansing products, astringent cleansers, makeup cleansers, liquid soaps, toilet soap bars, syndet bars and the like.

Examples skin care products include, but are not limited to hand/body/facial moisturizers, hand/body/facial creams, massage creams, hand/body/facial lotions, sunscreen products, tanning products, self-tanning products, aftersun products, masking products, lipsticks, lip gloss products, rejuvenating products, antiaging products, antiwrinkle products, anti-cellulite products, antiacne products and the like.

Examples shaving products include, but are not limited to shaving creams, aftershave products, preshave products and the like.

Examples deodorant/antiperspirant products include, but are not limited to deodorant products, antiperspirant products and the like.

A classification according to oral hygiene type would consist of, but is not limited to mouthwashes, pre-brushing dental rinses, post-bushing rinses, dental sprays, dental creams, toothpastes, toothpaste gels, toothpowders, dental cleansers, dental flosses, chewing gums, lozenges and the like.

A classification according to detergent, personal product and oral hygiene form would consist of aerosols, liquids, gels, creams, lotions, sprays, pastes, roll-on, stick, tablet, powdered and bar form.

A comprehensive list of essential and optional ingredients that are useful in detergent, personal product and oral hygiene compositions are described in McCutcheon's, Detergents and Emulsifiers (Vol 1) and McCutcheon's, Functional Materials (Vol 2), 1992 Annual Edition, published by McCutcheon's MC Publishing Co. as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference.

Industrial Application and Use

The heteroatom containing alkyl aldonamide compounds of the invention are useful as surfactants that may be used alone or in combination with other surfactants to provide improved foam and clarity. More specifically, the heteroatom containing alkyl aldonamide compounds of the invention are useful as foaming and solubilizing agents.

Furthermore, certain long chain heteroatom containing alkyl aldonamide compounds of the invention wherein the alkyl group contains 12 or more carbon atoms and certain long chain heteroatom containing alkyl aldobionamide compounds of the invention wherein the alkyl group contains 15 or more carbon atoms show less water solubility (Kf >60° C.) and are therefore useful as pearlescent agents, opacifiers and/or suspending agents.

The non-heteroatom containing alkyl aldonamide compounds of the invention wherein the alkyl group contains 9 carbons or more and certain non-heteroatom containing alkyl aldobionamide compounds of the invention wherein the alkyl group contains 15 carbons or more show the least water solubility and were also found to be useful as pearlescent agents, opacifiers and suspending agents.

The following Examples further describe and demonstrate the preferred embodiments that are within the scope of the present invention. The Examples are given solely for the purpose of illustration and are not to be construed as being limiting to the present invention since many variations are possible without departing from the spirit and scope of the invention.

EXAMPLES

Analysis of Monosaccharide Aldonamides by Gas Chromatography

Gas chromatography was found to be a convenient method for the examination of monosaccharide aldonamide compounds. The method of persilylation with hexamethyldisilazane (HMDS) and trimethylchlorosilane (TMCS) in pyridine is the simplest way for producing sufficiently stable and volatile derivatives for analysis. The mixture of both agents are more reactive than either reagent alone, and the by-products combine to form neutral ammonium chloride ($NH_4Cl$) or pyridine hydrochloride ($C_5H_5N \cdot HCl$).

The purity of several monosaccharide aldonamides were determined and found to be 97–99.9%. All products were well separated from starting materials, however aldonamides with alkyl chains containing eighteen carbons or more were not volatile enough for analysis.

Approximately 7–10 mg of a monosaccharide aldonamide compound was treated with 1 ml of sil-prep reagent (pyridine:HMDS:TMCS=9:3:1) in a 1 dram stoppered vial containing a magnetic stirring bar. The mixture was stirred vigorously at room temperature for about a hour or longer prior to chromatography. The solution became cloudy owing to precipitation of $NH_4Cl$ and $C_5H_5N \cdot HCl$ which was filtered through a CAMEO II 25 mm filter. From about 1.0 µl to about 1.1 µl of the resulting mixture was injected into the gas chromatograph.

All gas chromatography was conducted on a Hewlett Packard 5890 Series II Gas Chromatograph. All sample components were detected by a flame ionization detector using a split ratio of 100:1 and separated on a crosslinked 5% phenylmethyl silicone capillary column 25 m×0.32 mm×0.53 µm. The carrier gas was helium at 1 ml/minute and the temperature program was 3 minutes at 140° C. then 30° C./minute to 250° C. for 75 minutes.

Example 1 (No Heteroatom)

Preparation of Dodecyl D-Ribonamide (Used for Comparative Purposes)

A 200 ml four necked round bottom flask equipped with a condenser, addition funnel, thermometer and mechanical stirrer was charged with D-ribono-1,4-lactone (15.0 g, 0.10 mole) and methanol (45 g, for 43% total solids). The suspension was heated to 40°–43° C. for 15 minutes and the heating mantle removed. Dodecylamine (18.8 g, 0.10 mole) containing methanol (5 ml) was added dropwise over ½ hour. The reaction mixture was allowed to cool to room temperature (about 21° C.) followed by stirring overnight to allow complete crystallization. The white product was filtered, washed with methanol (3×20 ml) and dried under vacuum at 40°–45° C. giving 31.5 g (93% yield) of dodecyl D-ribonamide with a melting point of 101°–102° C. and 99.9% purity.

Example 2 (No Heteroatom)

Preparation of Coco D-Gluconamide (Used for Comparative Purposes)

A 5 liter four necked round bottom flask equipped with a condenser, addition funnel, thermometer and mechanical stirrer was charged with D-glucono-1,5-lactone (480.0 g, 2.69 moles) and methanol (2752 g, for 27% total solids). The suspension was heated to 40°–50° C. for 15 minutes and the heating mantle removed. Cocoamine (538.0 g, 2.69 moles) containing methanol (80 ml) was added dropwise over ½ hour. The reaction mixture was allowed to cool to room temperature (about 21° C.) followed by stirring overnight to allow complete crystallization. The white product was filtered, washed with methanol (3×500 ml) and dried under vacuum at 40°–45° C. giving 947.0 g (93% yield) of coco D-gluconamide with a melting point of 147°–148° C.

Examples 3–22 (No) Heteroatom)

The monosaccharide alkyl aldonamides (Examples 3–22) in Table 1 were prepared in a similar manner as in Example 2.

TABLE 1

Monosaccharide Alkyl Adlonamides
(Compounds Without Heteroatom for Comparative Purposes)

| Example | Structure | Attached Hydrocarbon | MP (°C.) | % Yield | % Purity |
|---|---|---|---|---|---|
| 3 | HOCH$_2$CHCHCHCHCNH— with OH, OH, OH, OH, O (D-Gluconamide) | C$_7$H$_{15}$ | 159–160 | 93 | 99.7 |
| 4 | D-Gluconamide | C$_8$H$_{17}$ | 159–160 | 90 | 99.9 |
| 5 | D-Gluconamide | C$_9$H$_{19}$ | 158–159 | 92 | 99.9 |
| 6 | D-Gluconamide | C$_{10}$H$_{21}$ | 157–158 | 91 | 99.9 |
| 7 | D-Gluconamide | C$_{11}$H$_{23}$ | 156–157 | 92 | 99.9 |
| 8 | D-Gluconamide | C$_{12}$H$_{25}$ | 155–156 | 96 | 99.9 |
| 9 | L-Gluconamide | C$_{12}$H$_{25}$ | 154–155 | 95 | 99.9 |
| 10 | D-Gluconamide | C$_{13}$H$_{27}$ | 155–156 | 95 | 99.9 |
| 11 | D-Gluconamide | C$_{14}$H$_{29}$ | 154–155 | 92 | 97.4 |
| 12 | D-Gluconamide | C$_{16}$H$_{33}$ | 152–153 | 94 | 99.9 |
| 13 | D-Gluconamide | C$_{18}$H$_{37}$ | 147–149 | 94 | — |
| 14 | D-Gluconamide | Tallow | 141–142 | 91 | — |
| 15 | D-Gluconamide | Soya | 135–137 | 86 | — |
| 16 | D-Gluconamide | Oleyl | 130–131 | 86 | — |
| 17 | HOCH$_2$CHCHCHCHCNH— with OH, OH, OH, OH, O (D-Galactonamide) | C$_{12}$H$_{25}$ | 187–188 (d) | 93 | 99.8 |
| 18 | HOCH$_2$CHCHCHCHCNH— with OH, OH, OH, OH, O (L-Galactonamide) | C$_{12}$H$_{25}$ | 187–188 (d) | 95 | 99.7 |
| 19 | HOCH$_2$CHCHCHCHCNH— with OH, OH, OH, OH, O (L-Mannonamide) | C$_{12}$H$_{25}$ | 159–160 | 95 | 99.6 |
| 20 | HOCH$_2$CHCHCHCHCHCNH— with OH, OH, OH, OH, OH, O (D-Glycero-L-Mannoheptonamide) | C$_{12}$H$_{25}$ | 195–197 (d) | 97 | 98.6 |

TABLE 1-continued

Monosaccharide Alkyl Adlonamides
(Compounds Without Heteroatom for Comparative Purposes)

| Example | Structure | Attached Hydrocarbon | MP (°C.) | % Yield | % Purity |
|---|---|---|---|---|---|
| 21 | HOCH$_2$CHCHCHCHCHCNH— with OH groups<br>D-Glucoheptonamide | C$_{12}$H$_{25}$ | 156–157 | 93 | 99.9 |
| 22 | HOCH$_2$CHCHCHCHCHCNH— with OH groups<br>D-Glucooctonamide | C$_{12}$H$_{25}$ | 156–157 | 93 | 99.9 | d = decomposition occurred during melting.

Example 23 (1 Ether Heteroatom)

Preparation of Octyl/Decyloxypropyl D-Ribonamide

A 250 ml four necked round bottom flask equipped with a condenser, additional funnel, thermometer and mechanical stirrer was charged with ribono-1,4-lactone (10.0 g, 0.07 mole) and methanol (37 g for 40% total solids). The suspension was heated to 40°–50° C. for 15 minutes and heating mantle removed. Octyl/decyloxypropylamine (14.6 g, 0.07 mole) was added dropwise over ½ hour and the reaction mixture stirred for six hours. The white product was filtered, washed with cold acetone (3×10 ml) and dried under vacuum at 40°–45° C. giving 14.0 g (57% yield) of octyl/decyloxypropyl D-ribonamide with a melting point of 71°–72° C. and 98.7% purity (62.8%/35.9%:C$_8$/C$_{10}$).

Examples 24–34 (1 Ether Heteroatom)

The monosaccharide alkyloxypropyl aldonamides (Examples 24–34) in Table 2 were prepared in a similar manner as in Example 23.

TABLE 2

Monosaccharide Alkyloxypropyl Aldonamides

| Example | Structure | Attached Hydrocarbon | MP (°C.) | % Yield | % Purity |
|---|---|---|---|---|---|
| 24 | HOCH$_2$CHCHCHCHCNH— with OH groups<br>D-Gluconamide | C$_3$H$_6$OCH$_2$CHC$_4$H$_9$<br>C$_2$H$_5$ | 89–90 | 73 | 99.9 |
| 25 | D-Gluconamide | C$_3$H$_6$OC$_8$H$_{17}$/C$_{10}$H$_{21}$ | 119–120 | 83 | 63.7/35.6 |
| 26 | D-Gluconamide | C$_3$H$_6$O-Isodecyl | 96–101 | 83 | — |
| 27 | D-Gluconamide | C$_3$H$_6$OC$_{12}$H$_{25}$ | 129–130 | 96 | 99.5 |
| 28 | D-Gluconamide | C$_3$H$_6$O-Isotridecyl | 81–86 | 74 | — |
| 29 | D-Gluconamide | C$_3$H$_6$OC$_{12}$H$_{25}$ to C$_{15}$H$_{31}$ | 125–126 | 82 | — |
| 30 | D-Gluconamide | C$_3$H$_6$OC$_{14}$H$_{29}$ | 129–130 | 86 | 99.7 |
| 31 | HOCH$_2$CHCHCHCHCHCNH— with OH groups<br>D-Glucoheptonamide | C$_3$H$_6$OC$_8$H$_{17}$/C$_{10}$H$_{21}$ | 129–130 | 88 | 66.2/33.6 |
| 32 | D-Glucoheptonamide | C$_3$H$_6$O-Isodecyl | 100–105 | 85 | — |
| 33 | D-Glucoheptonamide | C$_3$H$_6$OC$_{12}$H$_{25}$ | 133–134 | 89 | 99.9 |
| 34 | D-Glucoheptonamide | C$_3$H$_6$OC$_{12}$H$_{25}$ to C$_{15}$H$_{31}$ | 128–129 | 75 | — |

Example 35 (1 Ether Heteroatom)

Preparation of Octyl/Decyloxypropyl D-Glyceramide (No Solvent)

A 50 ml four necked round bottom flask equipped with a condenser, additional funnel, thermometer and mechanical stirrer was charged with methyl glycerate (5.1 g, 0.04 mole)

and octyl/decyloxypropylamine (8.0 g, 0.04 mole). The reaction mixture was heated to 65° C. for 24 hours. Isopropanol was added and the product was recrystallized, filtered, washed with cold isopropanol (3×5 ml) and dried under vacuum at 40°–45° C. giving 3.4 g (29% yield) of octyl/ decyloxypropyl D-glyceramide.

Example 36 (1 Ester Heteroatom)

Preparation of N-D-Gluconyl Dodecyl Glycinate

A 100 ml round bottom flask equipped with a condenser, addition funnel, thermometer and mechanical stirrer was charged with D-glucono-1,5-lactone (5.0 g, 0.03 mole) and isopropanol ( 35 g). The suspension was heated to 50° C. over 15 minutes. A mixture of glycine dodecyl ester p-toluenesulfonate salt (11.7 g, 0.03 mole), triethylamine (2.9 g 0.03 mole) and isopropanol (20 g) were added dropwise over 15 minutes from an addition funnel. The reaction mixture was stirred rapidly for about 2 hrs and then cooled to room temperature. The white product was filtered, washed with chloroform (3×150 ml) and dried under high vacuum at 35° C. giving 7.2 g (61% yield) of N-D-gluconyl dodecyl glycinate with a melting point of 121°–122° C. and 98.6% purity.

Example 37 (1 Ester Heteroatom)

Preparation of N-D-Gluconyl Dodecyl Ester of Ethanolamine

A 100 ml round bottom flask equipped with a condenser, addition funnel, thermometer and mechanical stirrer was charged with D-glucono1,5-lactone (7.0 g, 0.04 mole) and isopropanol (30 g). The suspension was heated to 65° C. over 15 minutes. A mixture of dodecyl ester of monoethanolamine p-toluenesulfonate salt (16.3 g, 0.04 mole), triethylamine (4.0 g 0.04 mole) and isopropanol (20 g) were added dropwise over 15 minutes from an addition funnel. The reaction mixture was stirred rapidly for about 6 hrs and then cooled to room temperature. The white product was filtered, washed with chloroform (3×150 ml) and dried under high vacuum at 35° C. giving 13.3 g (81% yield) of N-D-gluconyl dodecyl ester of ethanolamine with a melting point of 142°–143° C. and 97.4% purity.

Example 38 (1 Ester Heteroatom)

Preparation of N-D-Gluconyl Dodecyl DL-Alaninate

A 100 ml round bottom flask equipped with a condenser, addition funnel, thermometer and mechanical stirrer was charged with D-glucono-1,5-lactone (7.0 g, 0.04 mole) and isopropanol (30 g). The suspension was heated to 60° C. over 15 minutes. A mixture of DL-alanine dodecyl ester ptoluenesulfonate salt (16.9 g, 0.04 mole), triethylamine (4.0 g 0.04 mole) and isopropanol (20 g) were added dropwise over 15 minutes from an addition funnel. The reaction mixture was stirred rapidly for about 6 hrs and then cooled to room temperature. The white product was filtered, washed with chloroform (3×150 ml) and dried under high vacuum at 35° C. giving 12.5 g (73% yield) of N-D-gluconyl dodecyl alaninate with a melting point of 97°–98° C. and 98.8% purity.

Example 39 (1 Ester and 2 Ether Heteroatoms)

Preparation of N-D-Gluconyl Dodecyldi(oxyethyl) Glycinate

A 100 ml round bottom flask equipped with a condenser, addition funnel, thermometer and mechanical stirrer was charged with D-glucono-1,5-lactone (7.0 g, 0.04 mole) and isopropanol (30 g). The suspension was heated to 60° C. over 15 minutes. A mixture of glycine dodecyldi(oxyethyl) ester p-toluenesulfonate salt (20.2 g, 0.04 mole), triethylamine (4.0 g 0.04 mole) and isopropanol (20 g) were added dropwise over 15 minutes from an addition funnel. The reaction mixture was stirred rapidly for about 8 hrs and then cooled to room temperature. The white product was filtered, washed with chloroform (3×150 ml) and dried under high vacuum at 35° C. giving 8.9 g (43% yield) of N-D-gluconyl dodecyldi(oxyethyl) glycinate.

Example 40 (1 Amino Heteroatom)

Preparation of Cocoaminopropyl D-Gluconamide

A 1 liter round bottom flask equipped with a condenser, addition funnel, thermometer and mechanical stirrer was charged with D-glucono-1,5-lactone (100.0 g, 0.56 mole) and methanol (208 g for 55% total solids). The suspension was heated to 40° C. over 15 minutes and the heating mantle removed. Cocoaminopropylamine (153.8 g, 0.56 mole) was added dropwise over 15 minutes with rapid stirring. The reaction mixture was cooled and placed in a refrigerator at 0° C. overnight. The white product was filtered, washed with cold isopropanol (3×100 ml) and dried under high vacuum at 35° C. giving 206.0 g (81% yield) of cocoaminopropyl D-gluconamide with a melting point of 109°–111° C.

Example 41 (1 Amino Heteroatom)

Preparation of Hydrogenated Tallowaminopropyl D-Gluconamide

A 1 liter round bottom flask equipped with a condenser, addition funnel, thermometer and mechanical stirrer was charged with D-glucono-1,5-lactone (20.0 g, 0.11 mole) and methanol (56 g). The suspension was heated to 40° C. over 15 minutes and the heating mantle removed. Hydrogenated tallowaminopropylamine (36.0 g, 0.11 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 46.2 g (83% yield) of hydrogenated tallowaminopropyl D-gluconamide with a melting point of 112°–115° C.

Example 42 (1 Amino Heteroatom)

Preparation of Soyaaminopropyl D-Gluconamide

A 100 ml round bottom flask equipped with a condenser, addition funnel, thermometer and mechanical stirrer was charged with D-glucono-1.5-lactone (5.4 g, 0.03 mole) and methanol (7 g). The suspension was heated to 40° C. over 15 minutes and the heating mantle removed. Soya-aminopropylamine (10.0 g, 0.03 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 14.1 g (92% yield) of soyaaminopropyl D-gluconamide with a melting point of 97°–100° C.

Example 42 b (1 Amino Heteroatom)

Preparation of Oleylaminopropyl D-Gluconamide

A 500 ml round bottom flask equipped with a condenser, addition funnel, thermometer and mechanical stirrer was charged with D-glucono-1,5-lactone (25.0 g, 0.14 mole) and methanol (31 g). The suspension was heated to 40° C. over 15 minutes and the heating mantle removed. Oleylaminopropylamine (47.7 g, 0.14 mole) was added dropwise over 10 minutes and the reaction stirred for 6 hours. Acetone (300 ml) was added and the flask placed in a refrigerator overnight. The white solid was filtered, washed with cold acetone (3×50 g) and dried under vacuum at 35° C. giving 65.0 g (89% yield) of oleylaminopropyl D-gluconamide with a melting point of 100° C. –103° C.

Examples 43–44 (1 Amino and 1 Ether Heteroatom)

The monosaccharide alkyloxypropylaminopropyl aldonamides (Examples 43–44) in Table 3 were prepared in a similar manner as in Example 42.

Example 46 (1 Amide and 1 Ether Heteroatom)

Preparation of Dodecyl Pentadecyloxypropylacetamidopropyl D-Gluconamide in Solvent A 50 ml round bottom flask equipped with a condenser, addition funnel, thermometer and mechanical stirrer was charged with dodecyl to pentadecyloxypropylaminopropyl D-gluconamide (1.0 g, $2.93 \times 10^{-3}$ mole) and methanol (5 g). The suspension was heated to 40° C. and acetic anhydride (1.2 g, $1.18 \times 10^{-2}$ mole) was added dropwise over 15 minutes with rapid stirring. The reaction mixture was heated at 40° C. for 48 hours and the solvent, acetic acid and excess anhydride was removed by vacuum distillation (1.1 g, 98% yield). Water was added (3.6 g) to the reaction mixture and the product neutralized to a pH of about 7 with 0.1N sodium hydroxide solution. Hydrogen peroxide 3% (0.5 ml) was added and the product stirred for several hours. The sample is a pureable liquid ready for formulation.

TABLE 3

Monosaccharide Alkyloxypropylaminopropyl Aldonamides

| Example | Structure | Attached Hydrocarbon | MP (°C.) | % Yield |
|---|---|---|---|---|
| 43 | HOCH$_2$CHCHCHCHCNH— <br> \|  \|  \|  \|  \|\| <br> OH OH OH OH O <br><br> D-Gluconamide | C$_3$H$_6$NHC$_3$H$_6$O-Isotridecyl | 70–77 | 84 |
| 44 | D-Gluconamide | C$_3$H$_6$NHC$_3$H$_6$OC$_{12}$H$_{25}$ to C$_{15}$H$_{31}$ | 91–95 | 87 |

Example 45 (1 Amide Heteroatom)

Preparation of Hexylamido-2-Methylpentyl D-Gluconamide and Hexylamido-4-Methylpentyl D-Gluconamide A 100 ml round bottom flask equipped with a condenser, addition funnel, thermometer and mechanical stirrer was charged with D-glucono-1,5-lactone (6.7 g, 0.04 mole) and isopropanol (35 g). The suspension was heated to 50° C. over 25 minutes and the heating mantle removed. A mixture of hexylamido-2-methylpentylamine and hexylamido-4-methylpentylamine (45%/55%, 8.0 g, 0.04 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 7.6 g (52% yield) of hexylamido-2-methylpentyl D-gluconamide and hexylamido-4-methylpentyl D-gluconamide.

Examples 46–51 (Processing)

Examples 46–51 illustrate the process of manufacture of the invention.

Example 47 (1 Amide and 1 Ether Heteroatom)

Preparation of Dodecyl to Pentadecyloxypropylpropionamidopropyl D-Gluconamide in Water A 50 ml round bottom flask equipped with a condenser, addition funnel, thermometer, pH meter and mechanical stirrer was charged with dodecyl to pentadecyloxypropylaminopropyl D-gluconamide (1.0 g, $2.93 \times 10^{-3}$ mole) and water (4.0 g). Propionic anhydride (0.95 g, $7.33 \times 10^{-3}$ mole) is added portionwise along with 1N sodium hydroxide (which is added to maintain a pH of 7) at room temperature (21° C.). The mixture was stirred for 24 hours at room temperature and hydrogen peroxide 3% (0.5 ml) was then added. The sample is a pureable liquid ready for formulation.

Example 48 (1 Amide and 1 Ether Heteroatom)

Preparation of Dodecyl to Pentadecyloxypropyltrifluoroacetamidopropyl D-Gluconamide in Solvent A 50 ml plastic beaker equipped with an addition funnel, thermometer and stir bar was charged with dodecyl to pentadecyloxypropylaminopropyl D-gluconamide (1.0 g, 2.93×10$^{-3}$ mole) and methanol (15 g). The suspension was heated to 25° C. and trifloroacetic anhydride (1.2 g, 5.86×10$^{-3}$ mole) was added dropwise over 15 minutes with rapid stirring. The reaction mixture was stirred at room temperature for 8 hours and the solvent, trifluoroacetic acid and excess anhydride was removed by nitrogen sparge (1.4 g). Water (4.6 g) was added to the reaction mixture and the solution neutralized to a pH of about 7 with 0.1N sodium hydroxide solution. Sodium borohydride (0.03 g) was added and the product stirred for several hours. The sample is a pureable liquid ready for formulation.

Example 49 (1 Amide and 1 Ether Heteroatom)

Preparation of Dodecyl to Pentadecylopropylcaproamidopropyl D-Gluconamide from a Mixed Anhydride in Solvent A 50 ml round bottom flask equipped with a condenser, addition funnel, thermometer and mechanical stirrer was charged with dodecyl to pentadecyloxypropylaminopropyl D-gluconamide (2.0 g, 5.86×10$^{-3}$ mole) and methanol (30 g). A separate 50 ml round bottom flask equipped with a stir bar and nitrogen blanket was charged with caproic acid (0.68 g, 5.86×10$^{-3}$ mole), triethylamine (0.60 g, 5.86×10$^{-3}$ mole) and diethyl ether (10 g). This mixture was stirred at 0° C. and ethyl chloroformate (0.64 g, 5.91×10$^{-3}$ mole) was added rapidly. After about 0.5 hour the resulting ethyl hydrogen carbonate caproic anhydride was filtered, washed with ether (3 ml) and added to methanolic solution containing dodecyl to pentadecyloxypropylaminopropyl D-gluconamide. The reaction mixture was stirred at 40° C. for 2 hours and the solvent was removed by vacuum distillation (2.3 g 91% yield). Water was added to the reaction mixture and the solution neutralized to a pH of about 7 with 0.1N sodium hydroxide solution. About 0.5 ml of 3% hydrogen peroxide was added and the product stirred for several hours. The sample is a pureable liquid ready for formulation.

Example 50 (1 Amide and 1 Ether Heteroatom)

Preparation of Dodecyl to Pentadecyloxypropylpropionamidopropyl D-Lactobionamide in Solvent A 50 ml round bottom flask equipped with a condenser, addition funnel, thermometer and mechanical stirrer was charged with dodecyl to pentadecyloxypropylaminopropyl D-lactobionamide (3.0 g, 4.40×10$^{-3}$ mole) and methanol (20 g). The suspension was heated to 35° C. and propionic anhydride (1.7 g, 1.32×10$^{-2}$ mole) was added dropwise over 15 minutes with rapid stirring. The reaction mixture was heated at room temperature for 24 hours and the solvent, propionic acid and excess anhydride was removed by vacuum distillation (3.1 g, 95% yield).

Example 51 (1 Amide Heteroatom)

Preparation of Cocolauramidopropyl D-Lactobionamide in Solvent

A 250 ml round bottom flask equipped with a condenser, addition funnel, thermometer and mechanical stirrer was charged with cocoaminopropyl D-lactobionamide (15.8 g, 2.57×10$^{-2}$ mole), methanol (200 ml) and lauric anhydride (15.0 g, 3.92×10$^{-2}$ mole). The mixture was stirred and heated at 50° C. for several hours, then at room temperature for several days. The solvent was removed by rotaevaporation and the mixture slurried with ethyl acetate (100 ml), filtered and washed with ethyl acetate (2×90 ml) followed by air drying. The solid residue was then extracted with butanol (400 ml) and acidic water (400 ml). The butanol layer was separated and extracted with water ( 2×200 ml) containing sodium chloride followed by drying over magnesium sulfate. The dry butanol layer was filtered and washed with additional butanol (2×50 ml) which was removed by vacuum distillation giving 9.7 g (48% yield)of cocolauramidopropyl D-lactobionamide

Example 52 (No Heteroatom)

Preparation of Nonyl D-Lactobionamide (Used for Comparative Purposes)

A 100 ml round bottom flask equipped with a condenser, addition funnel, thermometer and mechanical stirrer was charged with D-lactobiono-1.5-lactone (100.0 g, 0.29 mole-)and methanol (300 g). The suspension was heated to 50° C. over 15 minutes. Nonylamine ( 39.1 g, 0.27 mole) was added dropwise over 15 minutes with rapid stirring. The reaction mixture was cooled to room temperature and stirred overnight. The product was filtered, washed with cold methanol (1×100 ml) and dried under vacuum at 35° C. The product was then recrystallized in methanol giving 110.0 g (84% yield) of nonyl D-lactobionamide with a melting point of 149°–150° C.

Examples 53–66 (No Heteroatom)

The disaccharide alkyl aldonamides (Examples 53–66) in Table 4 were prepared in a similar manner as in Example 52.

TABLE 4

| | Disaccharide Alkyl Aldobionamides (Compounds Without Heteroatom for Comparative Purposes) | | | | |
|---|---|---|---|---|---|
| Example | Structure | Attached Hydrocarbon | MP (°C.) | % Yield | % Purity (HPLC) |
| 53 | D-Lactobionamide | $C_{10}H_{21}$ | 138–139 | 47 | 99.0 |
| 54 | D-Lactobionamide | $C_{11}H_{23}$ | 147–148 | 34 | 99.2 |
| 55 | D-Lactobionamide | $C_{12}H_{25}$ | 137–138 | 35 | 99.3 |
| 56 | D-Lactobionamide | $C_{13}H_{27}$ | 147–148 | 36 | 99.9 |
| 57 | D-Lactobionamide | $C_{14}H_{29}$ | 126–127 | 92 | 97.4 |
| 58 | D-Lactobionamide | $C_{15}H_{31}$ | 147–148 | 70 | 99.3 |
| 59 | D-Lactobionamide | $C_{16}H_{33}$ | 130–131 | 60 | 99.3 |
| 60 | D-Lactobionamide | $C_{18}H_{37}$ | 112–113 | 92 | — |
| 61 | D-Lactobionamide | Tallow | 109–111 | 65 | 97.5 |

TABLE 4-continued

Disaccharide Alkyl Aldobionamides
(Compounds Without Heteroatom for Comparative Purposes)

| Example | Structure | Attached Hydrocarbon | MP (°C.) | % Yield | % Purity (HPLC) |
|---|---|---|---|---|---|
| 62 | D-Lactobionamide | Oleyl | 104–106 | 71 | — |
| 63 | D-Maltobionamide | $C_{11}H_{23}$ | 109–110 | 26 | 99.7 |
| 64 | D-Maltobionamide | $C_{12}H_{25}$ | 114–115 | 26 | 99.7 |
| 65 | D-Maltobionamide | $C_{14}H_{29}$ | 118–119 | 31 | 99.7 |
| 66 | D-Maltobionamide | $C_{16}H_{33}$ | 122–123 | 67 | 98.0 |

Example 67 (1 Ether Heteroatom)

Preparation of Octyl/Decyloxypropyl D-Lactobionamide

A 2 liter round bottom flask equipped with a condenser, addition funnel, thermometer and mechanical stirrer was charged with D-lactobion-1,5-lactone (84.1 g, 0.25 mole), methanol. (250 g for 35% total solids) and methanesulfonic acid (3 drops). The suspension was heated to 50° C. over 15 minutes and the heating mantle removed. Octyl/decyloxypropylamine (50.0 g, 0.25 mole) was added dropwise over 15 minutes with rapid stirring. The reaction mixture was cooled and stirred at room temperature overnight with 30% hydrogen peroxide (1 ml). Methanol was removed by vacuum distillation and acetone (1000 ml) added. The white product was filtered, washed with cold acetone (3×250 ml) and dried under high vacuum at 35° C. giving 112.2 g (84% yield) of octyl/decyloxypropyl D-lactobionamide with a melting point of 99°–101° C.

Example 68 (1 Ether Heteroatom)

Preparation of Dodecyloxypropyl D-Lactobionamide

A 3 liter round bottom flask equipped with a condenser, addition funnel, thermometer and mechanical stirrer was charged with D-lactobiono-1,5-lactone (180.0 g, 0.53 mole) and methanol (1100 ml). The suspension was heated to 50° C. over 15 minutes and the heating mantle removed. Dodecyloxypropylamine (128.8 g, 0.53 mole) was added dropwise over 30 minutes with rapid stirring. The reaction mixture was cooled and stirred at room temperature overnight. The white product was filtered, washed with cold acetone (2×400 ml) and dried under high vacuum at 40° C. giving 224.5 g (73% yield) of dodecyloxypropyl D-lactobionamide with a melting point of 117°–118° C.

Example 69 (1 Ether Heteroatom)

Preparation of Dodecyloxypropyl D-Maltobionamide

A 100 ml round bottom flask equipped with a condenser, addition funnel, thermometer and mechanical stirrer was charged with D-maltobiono-1,5-lactone (6.0 g, 0.02 mole) and methanol (25 ml). The suspension was heated to 50° C. over 15 minutes and the heating mantle removed. Dodecyloxypropylamine (4.3 g, 0.02 mole) was added dropwise over 30 minutes with rapid stirring. Acetone (50 ml) was added and the reaction mixture stirred at room temperature overnight. The white product was filtered, washed with cold acetone (3×30 ml) and dried under high vacuum at 30° C. giving 5.9 g (57% yield) of dodecyloxypropyl D-maltobionamide.

Example 70 (1 Ether Heteroatom)

Preparation of Dodecyl to Pentadecyloxypropyl D-Lactobionamide

A 2 liter round bottom flask equipped with a condenser, addition funnel, thermometer and mechanical stirrer was charged with D-lactobion-1,5-lactone (65.2 g, 0.19 mole), methanol (214 g for 30% total solids) and methanesulfonic acid (3 drops). The suspension was heated to 50° C. over 15 minutes and the heating mantle removed. Dodecyl to pentadecyloxypropylamine (50.0 g, 0.19 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 98.7 g (86% yield) of dodecyl to pentadecyloxypropyl D-lactobionamide with a melting point of 95°–98° C.

Example 71 (1 Ether Heteroatom)

Preparation of Tetradecyloxyropyl D-Lactobionamide

A 5 liter round bottom flask equipped with a condenser, addition funnel, thermometer and mechanical stirrer was charged with D-lactobiono-1,5-lactone (500.0 g, 1.47 moles)and methanol (3000 ml). The suspension was heated to 50° C. over 30 minutes and the heating mantle removed. Tetradecyloxypropylamine (401.7 g, 1.47 mole) was added dropwise over 30 minutes with rapid stirring. The reaction mixture was cooled and stirred at room temperature overnight. The white product was filtered, washed with cold acetone (2×700 ml) and dried under high vacuum at 40° C. giving 656.1 g (73% yield) of tetradecyloxypropyl D-lactobionamide.

Example 72 (1 Ester Heteroatom)

Preparation of N-D-Lactobionyl Dodecyl Glycinate

A 50 ml round bottom flask equipped with a condenser, thermometer and mechanical stirrer was charged with dodecyl glycinate hydrochloride (9.0 g, 0.03 mole) and 2.0M methanolic ammonia (16 ml, 0.03 mole). The mixture was stirred at room temperature for 10 minutes and lactobiono-1,5-lactone (10.9 g, 0.03 mole) added followed by heating at reflux for 1 hour. Activated charcoal was then added and the reaction mixture stirred for 15 minutes at reflux. Activated charcoal was removed by filtration over a bed of celite while warm, washed with methanol (3×50 ml) and the filtrate allowed to cool to room temperature. The solvent was removed by rotary evaporation, the product washed with ethyl ether (2×100 ml), filtered and dried in a vacuum oven at room temperature over phosphorous pentoxide giving 14.0 g (75% yield) of N-D-lactobionyl dodecyl glycinate.

Example 73 (1 Ester Heteroatom)

Preparation of N-D-Lactobionyl Dodecyl β-Alaninate

A 25 ml round bottom flask equipped with a condenser, thermometer and stir bar was charged with dodecyl β-alaninate hydrochloride (3.0 g, 0.01 mole) and 2.0M methanolic ammonia. (5 ml, 0.01 mole). The mixture was stirred at room temperature for 10 minutes and lactobiono-1,5-lactone (3.5 g, 0.01 mole) added followed by heating at reflux for 1 hour. Activated charcoal was then added and the reaction mixture stirred for 15 minutes at reflux. Activated charcoal was removed by filtration over a bed of celite while warm, washed with methanol (3×25 ml) and the filtrate allowed to cool to room temperature. The solvent was removed by rotary evaporation, the product washed with ethyl ether (2×50 ml), filtered and dried in a vacuum oven at room temperature over phosphorous pentoxide giving 4.3 g (70% yield) of N-D-lactobionyl dodecyl β-alaninate.

Example 74 (1 Amino Heteroatom)

Preparation of Cocoaminopropyl D-Lactobionamide

A 2 liter round bottom flask equipped with a condenser, addition funnel, thermometer and mechanical stirrer was charged with D-lactobion-1,5-lactone (66.4 g, 0.20 mole), methanol (175 g for 40% total solids) and methanesulfonic acid (3 drops). The suspension was heated to 50° C. over 15 minutes and the heating mantle removed. Cocoaminopropylamine (50.0 g, 0.20 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 96.9 g (83% yield) of cocoaminopropyl D-lactobionamide with a melting point of 97°–101° C.

Example 75 (1 Amino Heteroatom)

Preparation of Oleylaminopropyl D-Lactobionamide

A 2 liter round bottom flask equipped with a condenser, addition funnel, thermometer and mechanical stirrer was charged with D-lactobion-1,5-lactone (52.7 g, 0.15 mole), methanol (103 g for 50% total solids) and methanesulfonic acid (4 drops). The suspension was heated to 50° C. over 15 minutes and the heating mantle removed. Oleylaminopropylamine (50.0 g, 0.15 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 93.1 g (91% yield) of oleylaminopropyl D-lactobionamide with a melting point of 117°–118° C.

Example 76 (1 Amino Heteroatom)

Preparation of Hydrogenated Tallowaminopropyl D-Lactobionamide

A 1 liter round bottom flask equipped with a condenser, addition funnel, thermometer and mechanical stirrer was charged with D-lactobiono-1,5-lactone (20.0 g, 0.06 mole) and methanol (50 g). The suspension was heated to 400° C. over 15 minutes and the heating mantle removed. Hydrogenated tallowaminopropylamine (19.0 g, 0.06 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 46.2 g (84% yield) of hydrogenated tallowaminopropyl D-lactobionamide with a melting point of 135°–137° C.

Example 77 (1 Amino and 1 Ether Heteroatom)

Preparation of Dodecyl to Pentadecyloxypropylaminopropyl D-Lactobionamide

A 2 liter round bottom flask equipped with a condenser, addition funnel, thermometer and mechanical stirrer was charged with D-laetobion-1,5-lactone (53.6 g, 0.16 mole), methanol (104 g for 50% total solids) and methanesulfonic acid (3 drops). The suspension was heated to 50° C. over 15 minutes and the heating mantle removed. Dodecyl to pentadecyloxypropylaminopropylamine (50.0 g, 0.16 mole)was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 91.3 g (88% yield) of dodecyl to pentadecyloxypropylaminopropyl D-lactobionamide with a melting point of 107°–111° C.

Examples 78–80 (Processing)

Examples 78–80 illustrate the process of manucture of the invention.

Example 78 (6 Ether Heteroatoms)

Preparation of Dodecyl to Pentadecyloxypropyl D-Gluconamide Pentaoxyethylene ether A 100 g autoclave equipped with a pressure gauge, mechanical stirrer, rupture disk, gas inlet and gas outlet was charged with dodecyl to pentadecyloxypropyl D-gluconamide (7.0 g, $1.60 \times 10^{-2}$ mole) dissolved in dimethylformamide (30 g) and potassium hydroxide (0.04 g, $8.0 \times 10^{-4}$ mole). The autoclave was flushed with a blanket of nitrogen and a mild vacuum pulled. Ethylene oxide (3.5 g, $8.0 \times 10^{-2}$ mole) was then added and the mixture heated to 70° C.–100° C. for seven hours. The mixture was then cooled and discharged into a 100 ml round bottom flask equipped with a distillation head, thermometer and mechanical stirrer containing 30% hydrogen peroxide (0.5 ml). The mixture was stirred for several hours at 30° C. and then neutralized with 0.1N hydrochloric acid followed by removal of dimethylformamide by vacuum distillation giving 10.7 g of dodecyl to pentadecyloxypropyl D-gluconamide pentaoxyethylene ether.

Example 79 (5 Ether Heteroatoms)

Preparation of Dodecyloxypropyl D-Maltobionamide Tetraoxyethylene ether

A 100 g autoclave equipped with a pressure gauge, mechanical stirrer, rupture disk, gas inlet and gas outlet was charged with dodecyl oxypropyl D-maltobionamide (4.5 g, $7.49 \times 10^{-3}$ mole) dissolved in tert-butanol (20 g) and triethylamine (0.45 g, $4.45 \times 10^{-3}$ mole). The autoclave was flushed with a blanket of nitrogen and a mild vacuum pulled. Ethylene oxide (1.3 g, $3.0 \times 10^{-2}$ mole) was then added and the mixture heated to 70° C.–80° C. for seven hours. The mixture was then cooled and discharged into a 100 ml round bottom flask equipped with a distillation head, thermometer and mechanical stirrer containing 30% hydrogen peroxide (0.5 ml). The mixture was stirred for several hours at 30° C. and then neutralized with 1N hydrochloric acid followed by removal of tert-butanol by vacuum distillation giving 6.4 g of dodecyloxypropyl D-maltobionamide tetraoxyethylene ether.

Example 80 (11 Ether Heteroatoms)

Preparation of Dodecyloxypropyl D-Lactobionamide Octaoxyethylene Dipropylene Ether A 100 g autoclave equipped with a pressure gauge, mechanical stirrer, rupture disk, gas inlet and gas outlet was charged with dodecyl oxypropyl D-lactobionamide (7.0 g, $1.16 \times 10^{-2}$ mole) dissolved in dimethylformamide (30 g) and potassium hydroxide (0.03 g, $5.82 \times 10^{-4}$ mole). The autoclave was flushed with a blanket of nitrogen and a mild vacuum pulled. Ethylene oxide (4.1 g, $9.28 \times 10^{-2}$ mole) was then added and the mixture heated to 70° C.–100° C. for six hours. Propylene oxide (1.3 g, $2.32 \times 10^{-2}$ mole) was then added and the mixture heated to 70° C.–100° C. for additional five hours. The mixture was then cooled and discharged into a 100 ml round bottom flask equipped with a distillation head, thermometer and mechanical stirrer containing sodium borohydride (0.1 g). The mixture was stirred for several hours at 30° C. and then neutralized with 0.1N hydrochloric acid followed by removal of (dimethylformamide by vacuum distillation giving 12.5 g of dodecyl oxypropyl D-lactobionamide octaoxyethylenedipropylene ether.

Examples 81–84

Krafft Points and Foam Heights

Krafft Points

The temperature at and above which surfactants begin to form micelles instead of precipitates is referred to as the Krafft point ($T_k$) and at this temperature the solubility of a surfactant becomes equal to its CMC (numerical value at which micelles are formed).

The appearance and development of micelles are important since detergency (solubilization of soils) by dishwashing liquids, shampoos, detergents, etc., depend on the formation of these aggregates in solution.

The Krafft point was measured by preparing 650 ml of a 0.1% or 1.0% dispersion of aldonamide in water by weight. If the surfactant was soluble at room temperature, the solution was slowly cooled to 0° C. If the surfactant did not precipitate out of solution, its Krafft point was considered to be <0° C. (less than zero). If it precipitated out of solution, the temperature at which precipitation occurs was taken as the Krafft point.

If the surfactant was insoluble at :room temperature, the dispersion was slowly heated until the solution became homogeneous. It was then slowly cooled until precipitation occurred. The temperature at which the surfactant precipitates out of solution upon cooling was taken as the Krafft point.

Foam Height

Foam is an important attribute in many consumer products. It is one of the dominant factors that determines the commercial value of products such as dishwashing liquids, shampoos and soaps. Also, acceptability of many consumer products is closely related to the quality and texture of the foam they produce (psychological aspect).

Since most of the foaming data on surfactants is typically obtained by the Ross-Miles Foam Height Assay (Ross, J. and Miles, G. D. Am Soc. for Testing Material Method D1173-63 Philadelphia, Pa. (1953); Oil & Soap (1958) 62:1260) the foaming ability of these surfactants were acquired using this method.

In the Ross-Miles method, 200 mL of a surfactant solution contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette and then again after a given amount of time.

Using this method, the foam production (initial foam height in mm) and foam stability (final foam height after 10 minutes in mm) were measured at 0.1% aldonamide concentration, 40° C. and 0 ppm (parts per million) hardness. Aldonamides that were not soluble at 40° C. were measured at about 5°–10° C. above their Krafft points.

In order to show the unexpected enhancement in solubility and foam, applicants compound to a series of heteroatom containing alkyl aldonamide compound to a series of alkyl aldonamide compound having no heteroatom in the attached aliphatic group The results are as follows:

Example 81

| Monosaccharide Aldonamides Containing Four Hydroxyl Groups | | | | | |
|---|---|---|---|---|---|
| Entry | Compound | Average # of Hydrocarbons | Foam Height Initial (mm) | Foam Height Final (mm) | Krafft Point (0.1%), °C. |
| A | $C_{12}$ Ribonamide (Comparative) | 12 | 184 | 103 | 54 |
| B | $C_8/C_{10}$ Oxypropyl D-Ribonamide | 11.6 | 217 | 200 | 10 |

Example 82

| Monosaccharide Aldonamides Containing Five Hydroxyl Groups | | | | | |
|---|---|---|---|---|---|
| Entry | Compound | Average # of Hydrocarbons | Foam Height Initial (mm) | Foam Height Final (mm) | Krafft Point (0.1%), °C. |
| C | $C_7$ D-Gluconamide (Comparative) | 7 | 0 | 0 | <0 |
| D | $C_8$ D-Gluconamide (Comparative) | 8 | 0 | 0 | 12 |
| E | $C_9$ D-Gluconamide (Comparative) | 9 | 0 | 0 | 53 |
| F | $C_{10}$ D-Gluconamide (Comparative) | 10 | 199 | 6 | 75 |
| G | $C_{11}$ D-Gluconamide (Comparative) | 11 | X | X | 87 |
| H | $C_{12}$ D-Gluconamide (Comparative) | 12 | X | X | 91 |
| I | $C_{12}$ L-Gluconamide (Comparative) | 12 | X | X | 91 |
| J | $C_{12}$ D-Galactonamide (Comparative) | 12 | - Insoluble - | | >100 |
| K | $C_{12}$ L-Galactonamide (Comparative) | 12 | - Insoluble - | | >100 |
| L | $C_{12}$ L-Mannonamide (Comparative) | 12 | - Insoluble - | | >100 |
| M | $C_{14}$ D-Gluconamide (Comparative) | 14 | - Insoluble - | | >100 |
| N | $C_{16}$ D-Gluconamide (Comparative) | 16 | - Insoluble - | | >100 |
| O | $C_{18}$ D-Gluconamide (Comparative) | 18 | - Insoluble - | | >100 |
| P | Ethylhexyloxypropyl D-Gluconamide | 11 | 0 | 0 | <0 |
| Q | $C_8/C_{10}$ Oxypropyl D-Gluconamide | 11.6 | 212 | 165 | 48 |
| R | Iso $C_{10}$ Oxypropyl D-Gluconamide | 13 | 213 | 206 | <0 |
| S | $C_{12}$ Oxypropyl D-Gluconamide | 15 | 200 | 110 | 61 |
| T | Iso $C_{13}$ Oxypropyl D-Gluconamide | 16 | 190 | 100 | <15 |
| U | $C_{12}$–$C_{15}$ Oxypropyl D-Gluconamide | 16.3 | 200 | 110 | 58 |
| V | $C_{14}$ Oxypropyl D-Gluconamide | 17 | 203 | 101 | 53 |
| W | N-D-Gluconyl $C_{12}$ Glycinate | 14 | 183 | 107 | 63 |
| X | N-D-Gluconyl $C_{12}$ Ester of Ethanolamine | 14 | 185 | 111 | 63 |
| Y | N-D-Gluconyl $C_{12}$ DL-Alaninate | 15 | 197 | 112 | 53 |
| Z | N-D-Gluconyl $C_{12}$ Di(oxyethyl) Glycinate | 18 | 203 | 169 | <0 |
| AA | Cocoaminopropyl D-Gluconamide | 16 | 186 | 182 | 18 |
| BB | Soyaaminopropyl D-Gluconamide | 20.7 | 160 | 88 | <18 |
| CC | Oleylaminopropyl D-Gluconamide | 21 | 158 | 84 | <0 |
| DD | Iso $C_{13}$ Oxypropyl- aminopropyl D-Gluconamide | 19 | 180 | 178 | <0 |
| EE | $C_{12}$–$C_{15}$ Oxypropyl- | 19.3 | 180 | 176 | <0 |

-continued

| | Monosaccharide Aldonamides Containing Five Hydroxyl Groups | | | | |
|---|---|---|---|---|---|
| Entry | Compound | Average # of Hydrocarbons | Foam Height Initial (mm) | Foam Height Final (mm) | Krafft Point (0.1%), °C. |
| | aminopropyl D-Gluconamide | | | | |

X indicates low water solubility. foam height cannot be measured.

Example 83

| | Monosaccharide Aldonamides Containing Six to Seven Hydroxyl Groups | | | | |
|---|---|---|---|---|---|
| Entry | Compound | Average # of Hydrocarbons | Foam Height Initial (mm) | Foam Height Final (mm) | Krafft Point (0.1%), °C. |
| FF | $C_{12}$ D-Glucooctonamide (Comparative) | 12 | X | X | 86 |
| GG | $C_{12}$ D-Glycero-L-Mannoheptonamide (Comparative) | 12 | - Insoluble - | | >100 |
| HH | $C_{12}$ D-Glucoheptonamide (Comparative) | 12 | X | X | 91 |
| II | $C_8/C_{10}$ Oxypropyl D-Glucoheptonamide | 11.7 | 221 | 90 | 60 |
| JJ | Iso $C_{10}$ Oxypropyl D-Glucoheptonamide | 13 | 215 | 204 | 18 |
| KK | $C_{12}$ Oxypropyl D-Glucoheptonamide | 15 | 245 | 80 | 73 |
| LL | $C_{12}$–$C_{15}$ Oxypropyl D-Glucoheptonamide | 16.3 | 239 | 97 | 68 |

Example 84

| | Disaccharide Aldonamides Containing Eight Hydroxyl Groups | | | | |
|---|---|---|---|---|---|
| Entry | Compound | Average # of Hydrocarbons | Foam Height Initial (mm) | Foam Height Final (mm) | Krafft Point (1.0%), °C. |
| MM | $C_9$ D-Lactobionamide (Comparative) | 9 | 0 | 0 | 42 |
| NN | $C_{11}$ D-Lactobionamide (Comparative) | 11 | 0 | 0 | 61 |
| OO | $C_{12}$ D-Lactobionamide (Comparative) | 12 | 153 | 20 | 38 |
| PP | $C_{13}$ D-Lactobionamide (Comparative) | 13 | 145 | 78 | 70 |
| QQ | $C_{14}$ D-Lactobionamide (Comparative) | 14 | 141 | 59 | 18 |
| RR | $C_{14}$ D-Maltobionamide (Comparative) | 14 | 145 | 140 | 46 |
| SS | $C_{15}$ D-Lactobionamide (Comparative) | 15 | X | X | 84 |
| TT | $C_{16}$ D-Lactobionamide (Comparative) | 16 | 95 | 95 | 64 |
| UU | $C_{18}$ D-Lactobionamide (Comparative) | 18 | X | X | 82 |
| VV | $C_8/C_{10}$ Oxypropyl D-Lactobionamide | 11.6 | 168 | 158 | <0 |
| WW | $C_{12}$ Oxypropyl D-Lactobionamide | 15 | 165 | 154 | <0 |
| XX | $C_{12}$ Oxypropyl D-Maltobionamide | 15 | 163 | 155 | <0 |
| YY | $C_{12}$–$C_{15}$ Oxypropyl D-Lactobionamide | 16.3 | 166 | 155 | <0 |
| ZZ | $C_{14}$ Oxypropyl D-Lactobionamide | 17 | 163 | 154 | <0 |
| AAA | D-Lactobionyl $C_{12}$ Glycinate | 14 | 161 | 153 | <0 |
| BBB | D-Lactobionyl $C_{12}$ | 15 | 159 | 152 | <0 |

| Disaccharide Aldonamides Containing Eight Hydroxyl Groups | | | | |
|---|---|---|---|---|
| Entry | Compound | Average # of Hydrocarbons | Foam Height Initial (mm) | Foam Height Final (mm) | Krafft Point (1.0%), °C. |
| CCC | β-Alaninate Cocoaminopropyl D-Lactobionamide | 16 | 171 | 168 | <0 |
| DDD | Oleylaminopropyl D-Lactobionamide | 18 | 169 | 165 | <0 |
| EEE | $C_{12}$–$C_{15}$ Oxypropyl-aminopropyl D-lactobionamide | 19.3 | 173 | 169 | <0 |

X indicates low water solubility, foam height cannot be measured.

Detailed Discussion of Examples 81–84

From the above Tables (81–83), it can be clearly seen that monosaccharide alkyl aldonamide compounds lacking a heteroatom in the hydrocarbon chain (A, C-O, FF-HH) provide little or no foam and have significantly higher Krafft points. While not wishing to be bound by theory, it is believed that these compounds pack closely in the solid state through strong amide/hydroxyl hydrogen bonding and strong hydrocarbon Van der Waal forces. The net result is an unfavorable heat of hydration, high Krafft point, low or no water solubility and a poor foaming profile. Changing the stereochemistry (I-L) or increasing the hydrophilicity (FF-HH) of the sugar head group (by hydroxyl group addition) results in little or no improvement. However, monosaccharide alkyl aldonamide compounds that contain a heteroatom such as an oxygen (B, Q-V, II-LL), an ester (W-Y), an ester/oxygen combination (Z), a nitrogen (AA-CC) or a nitrogen/oxygen combination (DD, EE) in the hydrocarbon chain are believed to pack more loosely (favorably) in the solid state thereby resulting in a low Krafft point, increased water solubility and superior foaming profile. Also, closer comparison reveals that monosaccharide aldonamide compounds containing a heteroatom in the hydrocarbon chain unexpectedly allow the introduction of the same or greater alkyl chain length without sacrificing foaming and solubility characteristics. (Compare the average number of hydrocarbons of G-O to Q-EE and HH to II-LL).

Disaccharide alkyl aldobionamide compounds in Table 84 (MM-UU) tend to have reasonable Krafft points and foaming profiles. However, the addition of a heteroatom such as an oxygen (VV-ZZ), an ester (AAA, BBB), a nitrogen (CCC, DDD) or a nitrogen/oxygen combination in the hydrocarbon chain results in extremely low Krafft points (<0° C.), increased water solubility and enhanced foaming profile. Again, closer comparison reveals that disaccharide aldobionamide compounds containing a heteroatom in the hydrocarbon chain unexpectedly allow the introduction of the same or greater alkyl chain length without sacrificing foaming and solubility characteristics. (Compare the average number of hydrocarbons of OO-UU to VV-EE).

Thus, the ability of significantly improving the water solubility and foaming profile of an alkyl aldonamide or aldobionamide compound by heteroatom introduction is a significant achievement. These findings are quite unusual and unexpected, since monosaccharide alkyl aldonamide compounds are generally considered to be poor surfactants with poor emulsifying properties that are insoluble in water with little or no foaming capability. The monosaccharide alkyl aldonamide compounds are however, instead useful as pearlescent agents, opacifiers and/or suspending agents which require low water solubility.

Examples 85–91

Physical Chemistry of Heteroatom Containing Alkyl Aldonamide

Compounds

There are several unique characteristic properties that distinguish surface-active materials (surfactants) from other non-surface active materials. These include critical micelle concentration, surface tension reduction, efficiency in surface tension reduction, effectiveness in surface tension reduction, effectiveness of adsorption, area per molecule and micellar shape or structure. The following examples will show that the heteroatom containing alkyl aldonamide compounds of the invention are surface-active and are therefore considered to be a new class of sugar based surfactant.

Example 85

Critical Micelle Concentration

The critical micelle concentration (CMC) is defined as the concentration at which a surfactant forms micelles in aqueous solution. Micellization is the preferred interfacial phenomena, since certain surfactant benefits such as detergency (the solubilization of soils), foaming, wetting or emulsification depend on the formation of these aggregates in solution. Materials that do not form micelles do not provide any detergency, foaming, wetting or emulsification.

The CMC value of $C_8/C_{10}$ oxypropyl D-gluconamide was determined by plotting surface tension as a function of log(concentration) and extrapolating linear points to obtain an intersection point. The concentration at this point was taken as the CMC. The technique used was the Wilhelmy plate method and the instrument used was a Lauda Auto-Tensiometer. While wishing not to be bound to theory, it is believed that surfactants with low CMC values form micelles more readily at lower concentrations than those with high CMC values.

The critical micelle concentration (CMC) value of $C_8/C_{10}$ oxypropyl D-gluconamide (molecular weight=375.02 g/mole, 65.9% $C_8$, 34.1% $C_{10}$) was determined and is set forth below:

| | The Critical Micelle Concentration of $C_8/C_{10}$ Oxypropyl D-Gluconamide | | | |
|---|---|---|---|---|
| Entry | Surfactant | ANC* | CMC | Temperature (°C.) |
| 1 | $C_8/C_{10}$ Oxypropyl D-Gluconamide | 11.7 | 0.095 mM (0.0356%) | 60 |
| 2 | Dodecyl D-Gluconamide (Comparative) | 12.0 | None (Insoluble) | 60 |

(*) ANC = Average Number of Carbon Atoms in the Alkyl Chain

A necessary and sufficient condition for CMC formation and surface tension reduction is the presence of both hydrophilic and hydrophobic functional groups. The hydrophilic portion provides strong interaction between the surfactant at the interface and with the surrounding water phase. The hydrophobic portion provides spontaneous adsorption of the surfactant at the interface and strong interaction with the adjacent air phase. If any of these functions are not performed, then CMC formation and surface tension reduction will not occur. For significant surface activity, a properly balanced hydrophilic and hydrophobic character is essential. From the above table it can be seen that $C_8/C_{10}$ oxypropyl D-gluconamide is properly balanced and forms micelles at a surprising low critical micelle concentration whereas dodecyl D-gluconamide is insoluble in water and can not form micelles. This finding suggests that the heteroatom containing alkyl aldonamides of the invention to be surface-active and so these compounds are expected to deliver favorable surfactant benefits. Also, since dodecyl D-gluconamide is insoluble in water, the additional physical properties in Examples 86–91 of this compound can not be determined.

Example 86

Surface Tension Reduction

An important characteristic feature that surfactants have is the tendency for them to absorb at the water/air interface in an oriented manner, thereby altering the interfacial free energy of that surface. The surface free energy per unit area or surface tension ($\gamma$), is a measure of this work and may be considered as the minimum amount of work required to bring sufficient surfactant molecules to the surface.

The surface tension ($\gamma$) value of $C_8/C_{10}$ oxypropyl D-gluconamide was determined and is set forth below:

| Surface Tension of $C_8/C_{10}$ Oxypropyl D-Gluconamide at the Water/Air Interface | | | |
|---|---|---|---|
| Entry | Surfactant | $\gamma$ | Temperature (°C.) |
| 1 | $C_8/C_{10}$ Oxypropyl D-Gluconamide | 29.2 dyn/cm | 60 |
| 2 | Water | 60.2 dyn/cm | 60 |

From the above table it can be seen that $C_8/C_{10}$ oxypropyl D-gluconamide absorbs strongly at the water/air interface resulting in a significant reduction in water surface tension. This finding suggests that the heteroatom containing alkyl aldonamides of the invention to be surface-active and so these compounds are expected to deliver favorable surfactant benefits.

Examples 87–88

Performance of Heteroatom Containing Alkyl Aldonamide Compounds in

Reducing Surface Tension

For the purpose of comparing the performance of heteroatom containing alkyl aldonamide compounds in reducing surface tension to other surfactants, it is necessary to distinguish between the efficiency and effectiveness.

Efficiency of a surfactant in reducing surface tension is defined as the bulk phase surfactant concentration required to reduce the surface tension of water by some given amount.

Effectiveness of a surfactant in reducing surface tension is defined as the maximum reduction in surface tension that can be obtained regardless of the bulk phase surfactant concentration.

Example 87

Efficiency in Surface Tension Reduction

Since surface tension reduction depends on the replacement of water molecules at the interface by surfactant molecules, the efficiency of a surfactant in reducing interfacial tension should reflect the concentration of surfactant at the interface relative to that in bulk liquid phase. A suitable measure of efficiency with which a surfactant performs this function can be described as $pC_{20}$. This is defined as the negative logarithm of the bulk phase surfactant concentration necessary to reduce the surface tension of water by 20 dyn/cm and is given as:

$$pC_{20} = -\log[C_{(-\Delta\gamma=20)}] = -\log[C_{20}]$$

wherein:

$C(-\Delta\gamma=20)=C_{20}$ is the bulk phase surfactant concentration necessary to reduce the surface tension of water by 20 dyn/cm.

In general, $pC_{20}$ values are usually close to the minimum concentration needed to saturate the interface with surfactant molecules. While not wishing to be bound by theory, it is believed that surfactants that have high $pC_{20}$ values tend to absorb more efficiently at the interface thereby reducing the surface tension more efficiently than those that have low $pC_{20}$ values.

The efficiency of various surfactants in reducing surface tension ($pC_{20}$) were determined and are set forth below:

| The Efficiency of Various Nonionic Surfactants in Reducing the Surface Tension of Water | | | | |
|---|---|---|---|---|
| Entry | Surfactant | ANC* | $pC_{20}$ | Temperature (°C.) |
| 1 | $C_8/C_{10}$ Oxypropyl D-Gluconamide | 11.7 | 4.78 | 60 |
| 2 | Dodecytri(oxyethylene)Ether[1] $C_{12}H_{25}O(CH_2CH_2O)_3H$ (Comparative) | 12 | 5.34 | 25 |
| 3 | Dodecyltetra(oxyethylene) Ether[1] $C_{12}H_{25}O(CH_2CH_2O)_4H$ (Comparative) | 12 | 5.34 | 25 |
| 4 | Dodecylpenta(oxyethylene) Ether[1] | 12 | 5.37 | 25 |

-continued

The Efficiency of Various Nonionic Surfactants in Reducing the Surface Tension of Water

| Entry | Surfactant | ANC* | $pC_{20}$ | Temperature (°C.) |
|---|---|---|---|---|
| | $C_{12}H_{25}O(CH_2CH_2O)_5H$ (Comparative) | | | |
| 5 | Dodecylhepta(oxyethylene) Ether[1] | 12 | 5.26 | 25 |
| | $C_{12}H_{25}O(CH_2CH_2O)_7H$ (Comparative) | | 5.28 | 40 |
| | | | 5.41 | 60[2] |
| 6 | Dodecylocta(oxyethylene) Ether[1] | 12 | 5.20 | 25 |
| | $C_{12}H_{25}O(CH_2CH_2O)_8H$ (Comparative) | | 5.22 | 40 |
| | | | 5.39 | 60[2] |

[1] Rosen, M. J., in Surfactants and Interfacial Phenomena 2 ed., Wiley-Interscience Publication, 1989. pg 78: and Rosen, M. J., Cohen A. W., Dahanayake M. and Hua X. Y., J. Phys. Chem. 86, 541, 1981.
[2] This value was estimated by plotting temperature as function of $pC_{20}$ and extrapolating a linear line at 60° C.
(*) ANC = Average Number of Carbon Atoms in the Alkyl Chain From the above table it can be seen that $C_8/C_{10}$ oxypropyl D-gluconamide has a high $pC_{20}$ value and is expected to efficiently reduce the surface tension of water. This finding suggests that the heteroatom containing alkyl aldonamides of the invention to be surface-active and so these compounds are expected to deliver favorable surfactant benefits.

surfactant concentration increases. This will continue until the concentration reaches the critical micelle concentration (CMC), above which the surface tension remains nearly unchanged and the interface is saturated with surfactant. The surface tension at the CMC is therefore very close to the minimum interfacial tension or maximum surface pressure that the system can achieve. The surface pressure at this point, $\Pi_{cmc}$, is a suitable measure of the effectiveness of a surfactant in reducing surface tension and is given as:

$$\Pi_{cmc} = 20 + 2.3\, nRT(\Gamma_{max}) \log[CMC/C_{20}]$$

wherein:
n=1 which represents the number of ions whose surface concentration changes with the change in liquid phase surfactant concentration.
R=8.314×107 ergs/mol K (Gas Constant)
T=333.15K
$\Gamma_{max} = -\frac{1}{2} \cdot 303 RT (\partial\gamma/\partial\log [Conc])T = 3.85 \times 10^{-10}$ mole/cm$^2$
$CMC/C_{20}$=is the ratio of the critical micelle concentration to the bulk phase surfactant concentration necessary to reduce the surface tension of water by 20 dyn/cm.

While not wishing to be bound by theory, it is believed that surfactants that have higher $\Pi_{cmc}$ values tend to absorb effectively at the interface thereby reducing the surface tension of water more effectively than those with lower $\Pi_{cmc}$ values.

The effectiveness of various surfactants in reducing surface tension ($\Pi_{cmc}$) were determined and are set forth below:

Effectiveness of Various Nonionic Surfactants in Reducing the Surface Tension of Water

| Entry | Surfactant | $CMC/C_{20}$ | $\Pi_{cmc}$ | Temperature (°C.) |
|---|---|---|---|---|
| 1 | $C_8/C_{10}$ Oxypropyl D-Gluconamide | 5.7 | 38.5 dyn/cm | 60 |
| 2 | Dodecyltri(oxyethylene) Ether[1] | 11.4 | 44.1 dyn/cm | 25 |
| | $C_{12}H_{25}O(CH_2CH_2O)_3H$ (Comparative) | | 43.1 dyn/cm | 40 |
| | | | 41.4 dyn/cm | 60[2] |
| 3 | Dodecyltetra(oxyethylene) Ether[1] | 13.7 | 43.4 dyn/cm | 25 |
| | $C_{12}H_{25}O(CH_2CH_2O)_4H$ (Comparative) | 11.8 | 42.0 dyn/cm | 40 |
| | | | 40.7 dyn/cm | 60[2] |
| 4 | Dodecylpenta(oxyethylene) Ether[1] | 15.0 | 41.5 dyn/cm | 25 |
| | $C_{12}H_{25}O(CH_2CH_2O)_5H$ (Comparative) | | 41.2 dyn/cm | 40 |
| | | | 40.7 dyn/cm | 60[2] |
| 5 | Dodecylhepta(oxyethylene) Ether[1] | 14.9 | 38.3 dyn/cm | 25 |
| | $C_{12}H_{25}O(CH_2CH_2O)_7H$ (Comparative) | 13.9 | 38.5 dyn/cm | 40 |
| | | | 36.8 dyn/cm | 60[2] |
| 6 | Dodecylocta(oxyethylene) Ether[1] | 17.3 | 37.2 dyn/cm | 25 |
| | $C_{12}H_{25}O(CH_2CH_2O)_8H$ (Comparative) | 15.4 | 37.3 dyn/cm | 40 |
| | | | 36.3 dyn/cm | 60[2] |

[1] Rosen, M. J., in Surfactants and Interfacial Phenomena 2 ed., Wiley-Interscience Publication, 1989, pgs 146 and 224; and Rosen, M. J., Cohen A. W., Dahanayake M. and Hua X. Y., J. Phys. Chem. 86, 541, 1981.
[2] This value was estimated by plotting temperature as functon of surface pressure ($\Pi_{cmc}$) and extrapolating a linear line at 60° C.

Example 88

Effectiveness in Reducing Surface Tension

As mentioned before, surface tension reduction depends on the replacement of water molecules at the interface by surfactant molecules, therefore the effectiveness of a surfactant in reducing interfacial surface tension should reflect the saturated concentration of surfactant at the interface relative to that in bulk liquid phase. During this process the surface tension of water steadily decreases as bulk phase From the above table it can be seen that $C_8/C_{10}$ oxypropyl D-gluconamide has a high $\Pi_{cmc}$ value and is expected to effectively reduce the surface tension of water. For $C_8/C_{10}$ oxypropyl D-gluconamide, the surface pressure ($\Pi_{cmc}$) was found to be similar to dodecyltetra(oxyethylene) ether and dodecylpenta(oxyethylene) ether. This finding suggests that the heteroatom containing alkyl aldonamide compounds of the invention to be surface-active and so these compounds are; expected to deliver favorable surfactant benefits.

Example 89

Effectiveness of Adsorption at the Interface

The surface excess concentration at surface saturation ($\Gamma_{max}$) is defined as a measure of the effectiveness of surfactant adsorption at the water/air interface and represents the maximum value to which adsorption can be obtained. Effectiveness of adsorption is related to the interfacial area occupied by the surfactant molecule. The smaller the effective cross-sectional area of a surfactant at the interface, the greater its effectiveness of adsorption. The effectiveness of adsorption is an important factor in determining surfactant properties such as detergency, foaming, wetting or emulsification. While not wishing to be bound by theory, it is believed that surfactants that absorb effectively at the interface tend have tightly packed coherent interfacial films and often provide better surfactant benefits than those with loosely packed noncoherent films. The effectiveness of adsorption of $C_8/C_{10}$ oxypropyl D-gluconamide was determined using the Gibbs equation given as:

$$\Gamma_{max} = -1/2.303RT(\partial\gamma/\partial\log[Conc])_T$$

wherein:
$(\partial\gamma/\partial\log[Conc])_T = -24.574971$ ergs/cm$^2$ (which is equivalent to the
slope of a plot of $\gamma$ versus log[Conc]) R=8.3 14×10$^7$ ergs/mol K (Gas Constant)

T=333.15K

The surface excess concentration at surface saturation ($\Gamma_{max}$) of various surfactants were determined and are set forth below:

Effectiveness of Adsorption of Various Nonionic Surfactants at the Water/Air Interface

| Entry | Surfactant | $\Gamma_{max}$ | Temperature (°C.) |
|---|---|---|---|
| 1 | $C_8/C_{10}$ Oxypropyl D-Gluconamide | 3.85 × 10$^{-10}$ mole/cm$^2$ | 60 |
| 2 | Dodecyltri(oxyethylene) Ether[1] | 3.98 × 10$^{-10}$ mole/cm$^2$ | 25 |
|   | $C_{12}H_{25}O(CH_2CH_2O)_3H$ | 3.90 × 10$^{-10}$ mole/cm$^2$ | 40 |
|   | (Comparative) | 3.83 × 10$^{-10}$ mole/cm$^2$ | 60[2] |
| 3 | Dodecyltetra(oxyethylene) Ether[1] | 3.63 × 10$^{-10}$ mole/cm$^2$ | 25 |
|   | $C_{12}H_{25}O(CH_2CH_2O)_4H$ | 3.41 × 10$^{-10}$ mole/cm$^2$ | 40 |
|   | (Comparative) | 3.01 × 10$^{-10}$ mole/cm$^2$ | 60[2] |
| 4 | Dodecylpenta(oxyethylene) Ether[1] | 3.31 × 10$^{-10}$ mole/cm$^2$ | 25 |
|   | $C_{12}H_{25}O(CH_2CH_2O)_5H$ | 3.28 × 10$^{-10}$ mole/cm$^2$ | 40 |
|   | (Comparative) | 3.16 × 10$^{-10}$ mole/cm$^2$ | 60[2] |
| 5 | Dodecylhepta(oxyethylene) Ether[1] | 2.90 × 10$^{-10}$ mole/cm$^2$ | 25 |
|   | $C_{12}H_{25}O(CH_2CH_2O)_7H$ | 2.77 × 10$^{-10}$ mole/cm$^2$ | 40 |
|   | (Comparative) | 2.71 × 10$^{-10}$ mole/cm$^2$ | 60[2] |
| 6 | Dodecylocta(oxyethylene) Ether[1] | 2.52 × 10$^{-10}$ mole/cm$^2$ | 25 |
|   | $C_{12}H_{25}O(CH_2CH_2O)_8H$ | 2.46 × 10$^{-10}$ mole/cm$^2$ | 40 |
|   | (Comparative) | 2.40 × 10$^{-10}$ mole/cm$^2$ | 60[2] |

[1] Rosen, M. J., in Surfactants and Interfacial Phenomena 2 ed., Wiley-Interscience Publication, 1989, pg 78; and Rosen, M. J., Cohen A. W., Dahanayake M. and Hua X. Y., J. Phys. Chem. 86, 541, 1981.
[2] This value was estimated by plotting temperature as function of surface excess concentration at surface saturation ($\Gamma_{max}$) and extrapolating a linear line at 60° C.

From the above table it can be seen that $C_8/C_{10}$ oxypropyl D-gluconamide has a small cross sectional area resulting in a tightly packed coherent interfacial film and strong effective interfacial absorption. The surface excess concentration at surface saturation ($\Gamma_{max}$) of this compound was found to be similar to dodecyltri(oxyethylene) ether (a common non-ionic surfactant). This finding suggests that the heteroatom containing alkyl aldonamide compounds of the invention to be surface-active and so these compounds are expected to deliver favorable surfactant benefits.

Example 90

Area Per Molecule at the Interface

The area per molecule of a surfactant at the water/air interface provides information on the degree of packing and the orientation of the adsorbed surfactant molecule. While not wishing to be bound by theory, it is believed that surfactants that have small area per molecule values tend to pack more closely at the interface than those with large area per molecule values. From the surface excess concentration at surface saturation ($\Gamma_{max}$), the area per molecule ($a_m$) of $C_8/C_{10}$ oxypropyl D-gluconamide was determined and is given by:

$$a_m = 1\times10^{16}/N_{av}\Gamma_{max}$$

wherein:
$\Gamma_{max} = -\frac{1}{2}\cdot 303RT(\partial\gamma/\partial\log[Conc])_T$
$N_{AV} = 6.0221\times10^{23}$ per gram mole (Avogadro's Number)
T=333.15K The area per molecule ($a_m$) of several surfactants were determined and are set forth below:

Area Per Molecule of Various Nonionic Surfactants
at the Water/Air Interface

| Entry | Surfactant | $a_m$ | Temperature (°C.) |
|---|---|---|---|
| 1 | $C_8/C_{10}$ Oxypropyl D-Gluconamide | 43.1 Å$^2$ | 60 |
| 2 | Dodecyltri(oxyethylene) Ether[1] | 41.7 Å$^2$ | 25 |
|   | $C_{12}H_{25}O(CH_2CH_2O)_3H$ | 42.5 Å$^2$ | 40 |
|   | (Comparative) | 45.4 Å$^2$ | 60[2] |
| 3 | Dodecyltetra(oxyethylene) Ether[1] | 45.7 Å$^2$ | 25 |
|   | $C_{12}H_{25}O(CH_2CH_2O)_4H$ | 48.7 Å$^2$ | 40 |
|   | (Comparative) | 53.3 Å$^2$ | 60[2] |
| 4 | Dodecylpenta(oxyethylene) Ether[1] | 50.1 Å$^2$ | 25 |
|   | $C_{12}H_{25}O(CH_2CH_2O)_5H$ | 50.6 Å$^2$ | 40 |
|   | (Comparative) | 52.3 Å$^2$ | 60[2] |
| 5 | Dodecylhepta(oxyethylene) Ether[1] | 57.3 Å$^2$ | 25 |
|   | $C_{12}H_{25}O(CH_2CH_2O)_7H$ | 59.9 Å$^2$ | 40 |
|   | (Comparative) | 61.0 Å$^2$ | 60[2] |
| 6 | Dodecylocta(oxyethylene) Ether[1] | 66.0 Å$^2$ | 25 |
|   | $C_{12}H_{25}O(CH_2CH_2O)_8H$ | 67.4 Å$^2$ | 40 |
|   | (Comparative) | 69.0 Å$^2$ | 60[2] |

[1]Rosen, M. J., in Surfactants and Interfacial Phenomena 2 ed., Wiley-Interscience Publication, 1989, pg 78; and Rosen, M. J., Cohen A. W., Dahanayake M. and Hua X. Y., J. Phys. Chem. 86, 541, 1981.
[2]This value was estimated by plotting temperature as function of area per molecule ($a_m$) and extrapolating a linear line at 60° C.

From the above table it can be seen that $C_8/C_{10}$ oxypropyl D-gluconamide has a favorably small area per molecule value and is expected to pack tightly at the interface. The area per molecule ($a_m$) of this compound was found to be similar to dodecyltri(oxyethylene) ether. This finding suggests that the heteroatom compounds of the invention to be surface-active and so these compounds are expected to deliver favorable surfactant benefits.

Example 91

Micellar Shape and Structure

The shape or type of micelle produced by a surfactant in aqueous solution is an important criteria for delivering certain surfactant benefits such as viscosity, detergency, foaming, wetting or emulsification. At present there appears to be four major types of micelles a surfactant can form in aqueous solution;
(1) spherical micelles
(2) cylindrical rod-like micelles
(3) lamellar disk-like micelles
(4) vesicles or reversed micelles In aqueous media, surfactant molecules may be oriented in all these possible structures with their polar hydrophilic head groups pointed towards the aqueous phase and their non-polar hydrophobic alkyl chain groups pointed away from it. In general, surfactants with large bulky or loosely packed hydrophilic groups and long, thin hydrophobic groups tend to form predominately spherical micelles whereas those with small or tightly packed hydrophilic groups and bulky hydrophobic groups tend to form predominately cylindrical or lameliar micelles. Changes in temperature, concentration and functional groups in the surfactant may all cause a change in size or shape of a micelle.

A theory of micellar structure, based upon the geometry of various micelle shapes and the space occupied by the surfactant has been disclosed by J. N. Israelachvili, D. J. Mitchell and B. W. Ninham in the J. Chem. Soc. Faraday Trans. 2, 1525, 72, (1976) which is given as the packing parameter (p).

$$p = V_T/l_c(i\ a_m)$$

wherein;

$V_T = V_{(CH3)} + (n_c - 1)V_{(CH2)}$ and represents the volume occupied by the hydrophobic groups in the micellar core at a given temperature.

$l_c = 1.50 + 1.26\ n_c$ Å and represents the length of the hydrophobic group in the core.

$a_m$ = area per molecule or the cross-sectional area occupied by the hydrophilic group at the interface.
$V_{(CH3)} = 54.6 + 0.124\ (T-298°\ K.)Å^3$
$V_{(CH2)} = 26.9 + 0.0146\ (T-298°\ K.)Å^3$
$T = 333.15°\ K.$
$n_c$ = total number of carbons in the alkyl chain.

Values obtained from the packing parameter (p) represent the following structures:

| Values of (p) | Structure of Micelle in Aqueous Media |
|---|---|
| 0.00 to 0.33 | Spherical |
| 0.33 to 0.50 | Cylindrical |
| 0.50 to 1.00 | Lamellar |
| >1.00 | Reversed |

The packing parameter (p) of $C_8/C_{10}$ oxypropyl D-Gluconamide was determined as follows:

The Packing Parameter of $C_8/C_{10}$ Oxypropyl D-Gluconamide

| Entry | Surfactant | $n_a$[1] | $V_T(Å^3)$ | $l_c(Å)$[1] | $a_m(Å^2)$ | p |
|---|---|---|---|---|---|---|
| 1 | $C_8/C_{10}$ Oxypropyl D-Gluconamide | 12.7 | 379.7 | 17.5 | 43.1 | 0.503 |

[1]This value represents the number atoms in the alkyl chain and assumes that one oxygen atom is equivalent to one methylene group.

Form the above table it can be seen that the packing parameter (p) for $C_8/C_{10}$ oxypropyl D-gluconamide was found to be 0.503 which means that this compound is predicted to form cylindrical to lameliar micelles. This finding suggests that the heteroatom containing alkyl aldonamide compounds of the invention to be surface-active and so these compounds are expected to deliver favorable surfactant benefits.

This invention has been described with respect to certain preferred embodiments and various modifications and variations in the light thereof will be suggested to persons skilled in the art and are to be included within the spirit and purview of this application and the scope of the appended claims.

What is claimed is;

1. A process for producing an amido heteroatom containing alkyl aldonamide compound having at least one heteroatom in the alkyl chain, the process comprising the steps of:

(1) reacting an amino heteroatom containing alkyl aldonamide compound and an acid anhydride in 5 to 95% by weight water or 5 to 98% by weight organic solvent such that the molar ratio of acid anhydride to said amino heteroatom containing alkyl aldonamide compound is from about 7:1 to about 1:1;

(2) heating said acid anhydride and said amino heteroatom containing alkyl aldonamide mixture in the absence or presence of an organic or inorganic base at a temperature from about 0° C. to about 100° C. for about 0.5 to 96 hours; and (3) recovering said alkyl aldonamide product.

2. The process of claim 1 further comprising neutralizing the alkaline solution to a pH from about 6 to about 9 with an organic or inorganic acid to a pH from about 6 to about 9 selected from the group consisting of hydrochloric acid, sulfuric acid, oxalic acid, citric acid, formic acid, lactic acid, dodecylbenzenesulfonic acid, methanesulfonic acid and mixtures thereof.

3. A process according to claim 1, wherein the solvent is selected from the group consisting of methanol, ethanol, propanol, isopropanol, butanol, propylene glycol, ethylene glycol, diethylene glycol, polyethylene glycol, ethylene glycol monomethyl ether, ethylene glycol monoethyl ether, ethoxylated alcohol, acetone, methyl acetate, ethyl acetate, propyl acetate, isopropyl acetate, 2-methoxyethyl acetate, pentyl acetate and mixtures thereof.

4. A process according to claim 1, wherein the acid anhydride is selected from the group consisting of acetic anhydride, trifluoroacetic anhydride, propionic anhydride, butyric anhydride, valeric anhydride, caproic anhydride, $C_7$–$C_{18}$ alkyl anhydride, succinic anhydride, $C_1$–$C_{18}$ alkylsuccinic anhydride, $C_2$–$C_{18}$ alkylenesuccinic anhydride, maleic anhydride, ethyl hydrogen carbonate acetic anhydride, ethyl hydrogen carbonate butyl hydrogen carbonate propionic anhydride, ethyl hydrogen carbonate $C_7$–$C_{18}$ alkyl anhydride and mixtures thereof.

5. A process according to claim 1, wherein the molar ratio of acid anhydride to heteroatom containing alkyl aldonamide is from about 5:1 to about 1.1:1.

6. A process according to claim 1, wherein the molar ratio of acid anhydride to heteroatom containing alkyl aldonamide is from about 3.1 to about 1.2:1.

7. A process according to claim 1, wherein the temperature of the reaction is from about 10° C. to about 90° C.

8. A process according to claim 1, wherein the temperature of the reaction is from about 20° C. to about 80° C.

9. A process according to claim 1, wherein the aldonamide head group is selected from the group consisting of glyceramide, ribonamide, gluconamide, glucoheptonamide, lactobionamide, maltobionamide, ethoxylated gluconamide, propoxylated gluconamide, ethoxylated glucoheptonamide, propoxylated glucoheptonamide, ethoxylated lactobionamide, propoxylated lactobionamide, ethoxylated maltobionamide, propoxylated maltobionamide and mixtures thereof.

10. A process according to claim 1 wherein the reaction is carried out in the presence of water.

11. A process according to claim 10 wherein the reaction is carried out in the presence of an alkaline neutralizing agent.

12. A process according to claim 11 wherein the alkaline neutralizing agent is selected from the group consisting of inorganic hydroxides, metal alkoxides, inorganic carbonate salts, inorganic bicarbonate salts, organic ternary amines and mixtures thereof.

13. A process according to claim 11 wherein the alkaline neutralizing agent is selected from the group consisting of the sodium, potassium and ammonium salts of hydroxide, methoxide, ethoxide, carbonate, bicarbonate, acetate, oxalate; and monoethanolamine, diethanolamine, triethanolamine, triethylamine and mixtures thereof.

14. A process according to claim 1 wherein the water is not removed from the product.

15. A process according to claim 1 wherein water is removed from the final product by a method selected from the group consisting freeze drying, spray drying and vacuum distillation.

16. A process according to claim 1 wherein the reaction is carried out in the presence of aqueous organic solvent.

17. A process according to claim 1 wherein the aqueous solvent is not removed from the product.

18. A process according to claim 17 wherein the solvent is selected from the group consisting of propylene glycol, ethylene glycol, diethylene glycol, polyethylene glycol, ethanol, methanol, isopropanol, propanol, butanol, pentanol and mixtures thereof.

19. A process according to claim 1 wherein the solvent is removed from the product.

20. A process according to claim 1 wherein the reaction product is a syrup and additional organic solvent is added.

21. A process according to claim 20 wherein after additional solvent is added, the resulting product is filtered, washed with additional organic solvent and dried.

22. A process according to claim 1 wherein the product is solid and additional purification is achieved by:

(1) adding sufficient organic solvent and heat to dissolve the product;

(2) cooling until recrystallization;

(3) filtering and washing with organic solvent; and (4) drying.

23. A process according to claim 1 wherein additional purification is performed by column chromatography.

24. A process according to claim 23 wherein a solution of alkylamidoalkyl aldonamide is passed through a column containing an acidic ionic exchange resin followed by passing through a column containing a basic ionic exchange resin.

25. A process according to claim 1 wherein additional purification is performed by extraction from a mixture of water and organic solvent.

26. A process according to claim 1 wherein, after the anhydride and aldonamide are reacted, the product is treated with a bleaching agent.

27. A process according to claim 26, wherein the bleaching agent is selected from the group consisting of hydrogen peroxide, sodium hypochlorite, benzyl peroxide, peroxyformic acid, peroxyacetic acid, peroxytrifluoroacetic acid, peroxypropionic acid, peroxylauric acid, peroxymonosulfate and mixtures thereof.

28. A process according to claim 26, wherein the beaching agent or reducing agent is added at a level from about 0.01% to about 7% by weight of the total reaction mixture.

29. A process according to claim 26, wherein the beaching agent or reducing agent is added at a level from about 0.02% to about 5% by weight of the total reaction mixture.

30. A process according to claim 26, wherein the beaching agent or reducing agent is added at a level from about 0.03% to about 3% by weight of the total reaction mixture.

31. A process according to claim 1 wherein, after the anhydride and aldonamide are reacted, the product is treated with a reducing agent.

32. A process according to claim 31, wherein the reducing agent is selected from the group consisting of the sodium, potassium and calcium salts of bisulfite (hydrogen sulfite), borohydride, hydride and mixtures thereof.

33. A process according to claim 1 wherein the anhydride is of formula:

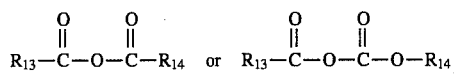

wherein $R_{13}$ and $R_{14}$ of the acid anhydride are the same or different, or may be combined to form a cyclic ring, and wherein the groups are selected from the group consisting of a straight or branched chain, saturated or unsaturated hydrocarbon radical; a straight or branched chain saturated or unsaturated hydrocarbon radical containing at least one oxygen heteroatom; a straight or branched chain saturated or unsaturated hydrocarbon radical substituted with a cycloaliphatic, aromatic or mixed aromatic group; a straight or branched chain saturated or unsaturated fluorocarbon radical; and mixtures thereof; wherein the total number of carbon atoms in $R_{13}$ and $R_{14}$ range from about 2 to about 18 in each radical.

34. A process for producing ethoxylated, propoxylated or ethoxylated/propoxylated derivatives of heteroatom containing alkyl aldonamide compounds having at least one heteroatom in the alkyl chain, the process comprising the steps of:

(1) preparing a homogeneous mixture comprising a heteroatom containing alkyl aldonamide compound, alkaline catalyst and an organic solvent;

(2) adding ethylene oxide, propylene oxide or mixtures thereof and said mixture to an autoclave flushed with nitrogen and heating at a temperature from about 60° C. to about 140° C. for about 0.5 to 96 hours; and (3) recovering the alkyl aldonamide compounds.

* * * * *